(12) United States Patent
Kennedy et al.

(10) Patent No.: US 8,535,709 B2
(45) Date of Patent: Sep. 17, 2013

(54) AGENTS FOR CONTROLLING BIOLOGICAL FLUIDS AND METHODS OF USE THEREOF

(75) Inventors: John P. Kennedy, Pooler, GA (US); Curtis E. Jones, II, Savannah, GA (US)

(73) Assignee: Southeastern Medical Technologies, LLC, Savannah, GA (US)

( * ) Notice: Subject to any disclaimer, the term of this patent is extended or adjusted under 35 U.S.C. 154(b) by 1840 days.

(21) Appl. No.: 11/452,139

(22) Filed: Jun. 13, 2006

(65) Prior Publication Data

US 2007/0053957 A1 Mar. 8, 2007

Related U.S. Application Data

(63) Continuation-in-part of application No. 11/009,623, filed on Dec. 13, 2004, and a continuation-in-part of application No. PCT/US2005/045034, filed on Dec. 13, 2005, and a continuation-in-part of application No. 11/452,090, filed on Jun. 12, 2006.

(60) Provisional application No. 60/750,096, filed on Dec. 13, 2005.

(51) Int. Cl.
*A61K 33/14* (2006.01)

(52) U.S. Cl.
USPC .......................................................... 424/443

(58) Field of Classification Search
None
See application file for complete search history.

(56) References Cited

U.S. PATENT DOCUMENTS

| | | | |
|---|---|---|---|
| 3,772,446 A | 11/1973 | Larsson | |
| 4,232,674 A | 11/1980 | Melican | |
| 4,331,653 A | 5/1982 | Brown et al. | |
| 4,505,935 A | 3/1985 | Larsson | |
| 4,557,935 A | 12/1985 | af Ekenstam et al. | |
| 4,759,354 A | 7/1988 | Quarfoot | |
| 4,931,284 A | 6/1990 | Ekman et al. | |
| 5,013,769 A * | 5/1991 | Murray et al. | 424/78.06 |
| 5,060,642 A | 10/1991 | Gilman | |
| 5,151,272 A | 9/1992 | Engstrom et al. | |
| 5,160,328 A | 11/1992 | Cartmell et al. | |
| 5,196,201 A | 3/1993 | Larsson et al. | |
| 5,300,358 A | 4/1994 | Evers | |
| 5,371,109 A | 12/1994 | Engstrom et al. | |
| 5,393,798 A | 2/1995 | Weber | |
| 5,478,355 A | 12/1995 | Muth et al. | |
| 5,531,925 A | 7/1996 | Landh et al. | |
| 5,550,145 A | 8/1996 | Olund et al. | |
| 5,586,971 A * | 12/1996 | Newman | 602/58 |
| 5,607,694 A | 3/1997 | Marx | |
| 5,620,702 A | 4/1997 | Podell et al. | |
| 5,631,019 A | 5/1997 | Marx | |
| 5,651,982 A | 7/1997 | Marx | |
| 5,686,097 A | 11/1997 | Taskovich et al. | |
| 5,736,152 A | 4/1998 | Dunn | |
| 5,753,252 A * | 5/1998 | Brown-Skrobot | 424/431 |
| 5,753,259 A | 5/1998 | Engstrom et al. | |
| 5,807,573 A | 9/1998 | Ljusberg-Wahren et al. | |
| 5,858,392 A | 1/1999 | Dumitriu et al. | |
| 5,906,831 A | 5/1999 | Larsson et al. | |
| 5,955,502 A | 9/1999 | Hansen et al. | |
| 6,162,241 A | 12/2000 | Coury et al. | |
| 6,217,897 B1 | 4/2001 | Buser | |
| 6,228,383 B1 | 5/2001 | Hansen et al. | |
| 6,312,725 B1 | 11/2001 | Wallace et al. | |
| 6,488,952 B1 | 12/2002 | Kennedy et al. | |
| 6,537,569 B2 | 3/2003 | Cruise | |
| 6,568,398 B2 | 5/2003 | Cohen | |
| 6,596,763 B1 * | 7/2003 | Thormar et al. | 514/506 |
| 6,599,517 B1 | 7/2003 | Ljusberg-Wahren et al. | |
| 6,660,278 B1 | 12/2003 | Larsson et al. | |
| 2006/0127437 A1 | 6/2006 | Kennedy et al. | |
| 2006/0275349 A1 | 12/2006 | Andrews et al. | |
| 2007/0059350 A1 | 3/2007 | Kennedy et al. | |

FOREIGN PATENT DOCUMENTS

| | | |
|---|---|---|
| WO | 96/39125 | 12/1996 |
| WO | 00/71183 | 11/2000 |
| WO | 03/057307 | 7/2003 |
| WO | 2006/065800 A2 | 6/2006 |
| WO | 2006/065800 A3 | 6/2006 |

OTHER PUBLICATIONS

Int'l Search Report for PCT/US2006/047514 dated May 2, 2008, six pages.
Written Opinion for PCT/US2006/047514 dated May 2, 2008, eight pages.
Sallam, A-S, et al "Formulation of an Oral Dosage Form Utilizing the Properties of Cubic Liquid Crystalline Phases of Glyceryl Monooleate", *European Journal of Pharmaceutics and Biopharmaceutics*, 53 (2002), pp. 343-352.
International Search Report, dated Aug. 7, 2006, Received Aug. 9, 2006, PCT/US2005/045034.

* cited by examiner

*Primary Examiner* — Brian-Yong Kwon
*Assistant Examiner* — Jennifer Berrios
(74) *Attorney, Agent, or Firm* — Nixon & Vanderhye PC

(57) ABSTRACT

Therapeutic formulations adapted for positive-pressure application for controlling biological fluid at a desired site in a subject, absorbent articles comprising therapeutic formulations, and anti-infective devices coated with therapeutic formulations, said formulations comprising about 25% to about 99% by weight liquid-crystal forming compound and 0% to about 75% by weight solvent. In addition, methods of using said formulations including methods for controlling biological fluid at a desired site in a subject, methods for controlling blood loss, and methods for facilitating effective closure of a vascular wound or incision site at a desired site in a subject are disclosed, the methods comprising administering particular formulations comprising liquid-crystal forming compounds and solvents that are described herein.

138 Claims, 13 Drawing Sheets

 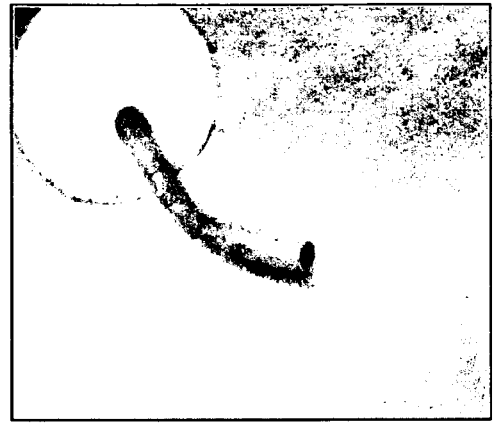
Fig. 4A    Fig. 4B
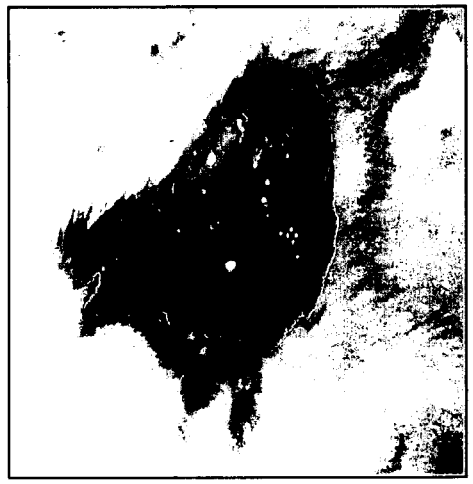 
Fig. 5A    Fig. 5B

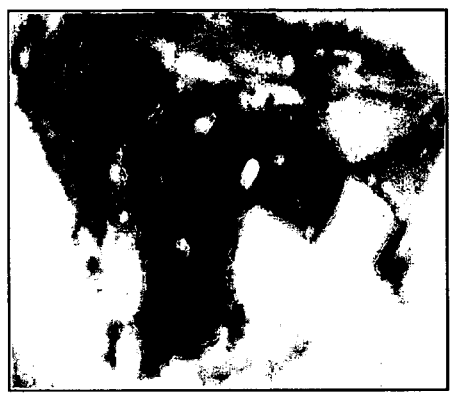 
Fig. 6A  Fig. 6B
 
Fig. 7A  Fig. 7B

 
Fig. 8A　　　　　　　　　　Fig. 8B
 
Fig. 9A　　　　　　　　　　Fig. 9B

AGENTS FOR CONTROLLING BIOLOGICAL FLUIDS AND METHODS OF USE THEREOF

CROSS REFERENCE TO RELATED APPLICATIONS

The present application claims priority from U.S. Provisional Application Ser. No. 60/750,096 filed Dec. 13, 2005 and is also a continuation-in-part of three pending applications: U.S. application Ser. No. 11/009,623 filed Dec. 13, 2004; PCT Application Serial No. PCT/US2005/045034 filed Dec. 13, 2005; and U.S. application Ser. No. 11/452,090 filed Jun. 12, 2006 by the same inventors. All of the foregoing applications are incorporated herein by reference in their entirety.

TECHNICAL FIELD AND

The present invention relates to compositions which are hydrophilic or amphiphilic and liquid crystalline formulations and methods for use as surgical adjunctive therapies, hemostatic agents, and as primary treatment modalities for hard and soft tissue wounds as well as the basis for cosmetic medical devices.

BACKGROUND ART

The use of hemostatic agents and devices is a common practice in modern surgery. The general field ranges from the use of agents exhibiting local action by the physical presence of the agent such as astringents (aluminum and magnesium salts), hydrolyzed gelatin (Gelfoam®—Pharmacia) and oxidized cellulose (Surgicel®—Johnson & Johnson) to products seeking to exploit physiologic mechanisms such as thrombin- and fibrin-based systems. However, the field is plagued with formulations of limited efficacy and systems that ultimately expose patients to greater risk of adverse immune response. Formulations that can be applied in a variety of physical states to quickly and reliably establish hemostasis without the risk of secondary immunologic responses would be highly desirable and of great commercial interest.

SUMMARY OF THE INVENTION

According to the present invention, new compositions are disclosed with a number of advantages over previously known compositions in the field. The inventors have discovered that at least in part by controlling biological fluids, certain formulations of liquid-crystal forming compounds demonstrate advantageous utilities including: promoting hemostasis; promoting wound healing; providing barriers to seal tissues and prevent adhesions; promoting tissue growth; mimicking soft tissues; and inhibiting microbial infections. Furthermore it has been discovered that: certain fatty acids, when added to certain formulations of liquid-crystal forming compounds, increase the viscosity or firmness of the highly viscous liquid crystal phase once formed; the compositions and formulations provide excellent toxicity, sensitization and irritation profiles; certain compositions may be designed to inhibit thrombin; the compositions may be designed for in situ activation; and certain compositions may be designed to be biodegradable; all of which support their use in medical practice.

In a first embodiment of the invention there is provided a therapeutic formulation adapted for positive-pressure application and effective for controlling biological fluid at a desired site in a subject, the formulation comprising about 25% to about 99% by weight liquid-crystal forming compound and 0% to about 75% by weight solvent, wherein the formulation effectively controls biological fluid at the desired site in the subject. In related embodiments, the solvent may be a polar solvent, a non-polar solvent, a semi-polar solvent or a combination thereof, and particular formulations may comprise about 97% liquid-crystal forming compound and about 3% normal saline solution; about 65% liquid-crystal forming compound and about 15% normal saline solution; about 35% liquid-crystal forming compound and about 65% normal saline solution; about 92.5% liquid-crystal forming compound, about 5% normal saline, and about 2.5% sodium hyaluronate; about 95% liquid-crystal forming compound and about 5% isopropyl myristate; about 95% liquid-crystal forming compound and about 5% 190 proof ethanol; or about 80% liquid-crystal forming compound and about 20% cottonseed oil.

Other particular embodiments may comprise platelets, platelet-rich plasma, plasma or whole blood, in addition to, or in place of, the above-mentioned solvents. Some particular embodiments may thus comprise about 97% liquid-crystal forming compound and about 3% whole blood; about 80% liquid-crystal forming compound and about 9% whole blood; about 65% liquid-crystal forming compound and about 15% whole blood; about 35% liquid-crystal forming compound and about 25% whole blood, about 97% liquid-crystal forming compound and about 3% blood plasma; about 65% liquid-crystal forming compound and about 15% blood plasma; or about 35% liquid-crystal forming compound and about 25% blood plasma.

In another embodiment, there is provided an absorbent article comprising an absorbent layer and a formulation effective for controlling biological fluid of a human or veterinary subject, wherein the formulation comprises from about 25% to 99% by weight liquid-crystal forming compound and about 0% to 75% by weight solvent and is present within or on at least a portion of the article. Related embodiments may comprise an absorbent layer that further includes an absorbent additive; a liquid-permeable and moisture vapor-permeable outer layer having an inner surface and an outer surface, the inner surface essentially coextensive with an outer surface of the absorbent layer; a liquid-impermeable and moisture vapor-permeable outer layer having an inner surface and an outer surface, the inner surface essentially coextensive with an outer surface of the absorbent layer; an absorbent article further comprising a liquid-impermeable and moisture vapor impermeable outer layer having an inner surface and an outer surface, the inner surface essentially coextensive with an outer surface of the absorbent layer; a liquid-permeable liner, adapted to be non-adherent to a wound, having a surface that is substantially coextensive with an inner surface of the absorbent layer such that the absorbent layer is located between the liquid-permeable liner and the outer layer; or any combination thereof.

In other embodiments, the composition effective for controlling biological fluids in the article provides utility as an anti-adherent between the article and bodily tissue to assist in placement or removal of the article from a site of use thereby reducing trauma from application or removal of said article, and the biological fluid controlling formulation may be applied to the article by spray coating, hot-melt coating, dip coating, direct transfer, manual application or a combination thereof. Specific embodiments provide an article that may be any of a wound dressing, a medical sponge, a hemostatic article, a hemostatic article for the nose, an adhesive bandage, a wound packing, an internal vascular closure packing, an external vascular closure dressing, a swellable absorbent article, a fibrotic wound packing article, or a feminine hygiene product, and the liquid-crystal forming compound may be any of a fatty acid ester, a polyethylene oxide, a glycolipid, a polyester, a polyethylene glycol, or a combination thereof. In related embodiments, the fatty acid ester may be a monoester, diester, triester or mixture thereof, and the monoester may be the group of glyceryl monoarachidonate, glyceryl monolaurate, glyceryl monolinoleate, glyceryl monolinolenate, glyceryl monomyristate, glyceryl monopalmitoleate, glyceryl monooleate, and glyceryl monostearate; glyceryl monocaprate, glyceryl monocaprylate, glyceryl monococoate, glyceryl monocollagenate, glyceryl monoerucate, glyceryl monohydroxystearate, glyceryl monoisopalmitate, glyceryl monolinoleate, glyceryl monolinolenate, glyceryl monomyristate, glyceryl monopalmitate, glyceryl monopentadecanoate, glyceryl monopolyacrylate, glyceryl monotallowate, glyceryl monothiopropionate, glyceryl monocundecylenate, isopropyl monoarachidonate, isopropyl monolaurate, isopropyl monolinoleate, isopropyl monolinolenate, isopropyl monomyristate, isopropyl monopalmitoleate, isopropyl monooleate, and isopropyl monostearate; methyl monoarachidonate, methyl monolaurate, methyl monolinoleate, methyl monolinolenate, methyl monomyristate, methyl monopalmitoleate, methyl monooleate, and methyl monostearate, propylene glycyl monoarachidonate, propylene glycyl monolaurate, propylene glycyl monolinoleate, propylene glycyl monolinolenate, propylene glycyl monomyristate, propylene glycyl monopalmitoleate, propylene glycyl monooleate, propylene glycyl monostearate or a combination thereof. For applications that optimally require highly viscous liquid crystalline states to be formed, fatty acid esters, phospholipids and glycolipids include the liquid-crystal forming compound that are preferable alone or in combination with others, glycerol monooleate, glycerol monoerucate, phosphatidylcholine and phosphatidylethanolamine providing more cost effective examples for applications requiring bulk quantities.

Another particular embodiment provides an infection resistant device, the device treated with an anti-infective formulation comprising about 25% to 99% by weight fatty acid or fatty acid ester, wherein said anti-infective formulation inhibits the formation of pathogen growth on the device, or in adjacent tissues, thereby imparting infection resistance to the device. In related embodiments, the anti-infective formulation may further comprise about 0% to 75% solvent and the fatty acid or fatty acid ester may be a liquid-crystal forming compound, and in some embodiments, upon formation of a liquid crystal, the anti-infective formulation becomes viscous and form fitting thereby lessening migration within or upon bodily tissues and attenuates clearance of the formulation from the site of device placement, or a site adjacent to or near to where the device is placed within or upon a subject. In still other embodiments, the liquid crystal formulation may act as a controlled-release delivery system of degradation products from the formulation, wherein said degradation products provide an additional anti-infective effect.

Related embodiments provide a device that is effective for treatment of an acute or chronic wound, and the acute wound may be an abrasion, burn, laceration, puncture or incision, and the chronic wound may be an ulceration including an ulcer of a leg, decubitus, fungal, diabetic, gastric, foot, sacral or indolent ulcer. In other embodiments, the device may be effective as a filler of a tissue void, including those created by trauma, disease or a surgical procedure, and more particularly, and in still other embodiments, the device may be treated with an anti-infective formulation by spray coating, hot-melt coating, dip coating or a combination thereof prior to use. In some embodiments, the device may be composed of organic material, inorganic material, or a combination thereof, and in still other embodiments, the device may be a catamenial absorption device, condom, prophylactic, medical sponge, surgical dressing, wound dressing, adhesive bandage or a combination thereof. Alternatively, the device may be a prosthetic, an implant or a combination thereof. In related embodiments, the prosthetic or implant type may be a spinal, orthopedic, dental, cardiac, neural, or cosmetic medical prosthetic or implant type, or a combination thereof. In particular embodiments, the orthopedic prosthetic or implant may be an artificial joint, fracture repair hardware, artificial cartilage, a plate, a screw, a nail, a wire or a combination thereof; the dental prosthetic or implant may be a root form, a Ramus frame, a transosseous implant, a blade form, fracture repair hardware, a prosthetic device, general hardware, a plate, a screw, a nail, a wire or a combination thereof; the cardiac prosthetic or implant may be a pacemaker, a defibrillator, a heart valve, a vascular graft or a combination thereof; and the cosmetic medical prosthetic or implant may be a breast implant, a dermal filler, a tissue void filler, a gluteal implant, a facial implant or a combination thereof.

Still other embodiments provide an infection resistant device, the device treated with an anti-infective formulation wherein the anti-infective formulation comprises about 25% to 99% liquid-crystal forming compound, about 0% to 50% fatty acid and about 0% to 50% solvent, by weight; about 90% liquid-crystal forming compound, about 5% lauric acid and about 5% solvent by weight; about 65% liquid-crystal forming compound, about 10% myristic acid and about 25% solvent, by weight; or about 35% liquid-crystal forming compound, about 15% palmitic and about 40% solvent, by weight.

Another embodiment provides a hemostatic formulation effective for controlling bleeding at a desired site in a human or veterinary subject, the composition comprising 25% to about 99% by weight liquid-crystal forming compound and 0% to about 75% by weight solvent, wherein the hemostatic formulation is adapted for positive pressure application upon or within tissue, effects hemostasis and induces local effects at the desired site within about 15 minutes or less, thereby controlling bleeding. More particularly, hemostasis may be effected and local effects induced at the site within about 10 minutes or less of application, still more particularly within about 5 minutes or less of application, still more particularly within about 2 minutes or less of application, and still more particularly within about 30 seconds or less of application.

In related embodiments of a hemostatic formulation, the solvent may be any of an alcohol, polyethylene glycol, propylene glycol, polypropylene glycol, water, isotonic aqueous solution, biological fluid, a physiologic buffered system, urine, saliva, serous fluid, synovial fluid, gastric secretions, cerebrospinal fluid, vitreous humor, lymph, wound exudate, cholesterol, a physiologic buffered system or combination thereof; the liquid-crystal forming compound may be any of a fatty acid, fatty acid monoester, fatty acid diester, fatty acid triester or combination thereof further comprising at least one unsaturated carbon-carbon bond. More particularly, the liquid crystal forming-agent may be a glyceryl monoester, diester, triester, or combination thereof, and still more particularly, the liquid-crystal forming compound may be glyceryl monooleate.

In general, the solvent of a given formulation may be any of a polar solvent, a non-polar solvent, a co-solvent system or combinations thereof including various alkanols, polyethylene glycol, propylene glycol, polypropylene glycol, glycol, water, isotonic aqueous solution, biological fluid, a physiologic buffered system, blood, urine, saliva, serous fluid, synovial fluid, gastric secretions, cerebrospinal fluid, sweat, tears, bile, chyme, mucous, vitreous humor, lymph, wound exudate, cholesterol or combination thereof; the liquid-crystal forming compound may be self assembling members selected from the group of a polymer and a material of biological significance, such as fatty acids, fatty acid esters, proteins, peptides, carbohydrates, glycolipids and lipids or combinations thereof further comprising at least one unsaturated carbon-carbon bond. More particularly, the liquid crystal forming-agent may be a glyceryl monoester, diester, triester, or combination thereof, and still more particularly, the liquid-crystal forming compound may be glyceryl monooleate. As envisioned and utilized, a solvent is not required for some applications of the formulations disclosed, particularly if the formulation is already in the liquid state or molten and a solvent will be made available or incorporated just prior to administration or acquired in situ.

Still yet another embodiment provides a formulation for a thrombin inhibitor comprised of about 25 to 99% by weight liquid-crystal forming compound and about 0% to 75% by weight solvent, wherein the formulation is adapted for positive pressure application to desired site of a subject. In related embodiments, the liquid-crystal forming compound may be a fatty acid ester. More particularly, the thrombin inhibitor formulation may be effective as a filler of a tissue void, such as those created by trauma, disease or a surgical procedure, and more particularly, the thrombin inhibitor formulation may also be a neuroprotective agent.

Another embodiment provides a cosmetic medical formulation effective for mimicking soft tissue at a desired site of a subject, the formulation comprising about 25% to 99% by weight liquid-crystal forming compound, about 0% to about 75% by weight solvent, and
other compounds, as required, to provide viscosities and textures effective for mimicking soft tissue. In related embodiments, the cosmetic medical formulation may further comprise an antioxidant, and the antioxidant may be a water soluble or oil soluble antioxidant, including any of ascorbic acid, ascorbic acid salts and esters, butylated hydroxyanisole, butylated hydroxytoluene, lecithin, isopropyl palmitate, isopropyl myristate, ubiquinol, phenolics, tocopherols, retinols, calciferols, thioglycolic acid, sulfur dioxide, cysteine hydrochloride, sulfites, ascorbic palmitates, alkyl gallates or any combination thereof.

Embodiments of the invention also provide that any of the disclosed formulations may further comprise an augmentative agent, a therapeutic agent or combinations thereof, including the following:
a hemostasis or coagulation promoting agent; a vasoactive agent; a tissue growth stimulant or a healing promoter; an anti-infective agent; an adhesive agent; a swelling agent; a viscosity enhancer; an anesthetic; a solvent or co-solvent; a thinning agent; a filler; an anti-oxidant; an anti-scarring or anti-inflammatory therapeutic agent; a physiologically compatible monovalent ion, divalent ion, trivalent ion or salt thereof; a bleaching agent; a miscellaneous therapeutic agent; a controlled-release component or composition; an embolism promoting material; or any combination thereof.

In particular embodiments of a formulation, the augmentative or therapeutic agent or combinations thereof may be any of a hemostasis or coagulation promoting agent including a nitric oxide or a nitric oxide generating agent, a catecholamine such as epinephrine, a phospholipid, gelatin, collagen, chitosan, glucosamines such as n-acetylglucosamine, an enzyme, an enzyme inhibitor, a fatty acid, a hormone, a silicone compound, bentonite, fumed silica, colloidal silica, micronized silica, diatomaceous earth, talc, titanium dioxide, potassium sulfate, aluminum sulfate, aluminum chloride, ammonium chloride, ferric sulfate, ferric sub sulfate, copper sulfate, an astringent, an exothermic compound (such as calcium bromide, calcium oxide or calcium chloride), a blood product (such as platelets, prothrombin, thrombin, fibrin, fibrinogen, thromboplastin or a clotting factor), whole blood, blood plasma; a vasoactive agent including a nitric oxide or nitric oxide generating agent, a vasoconstrictor, a cholinomimetic agent, an anticholinergic agent, a cholinergic blocker, a sympathomimetic, an antiadrenergic agent, an adrenergic blocker, an immunogenic agent, a hormone such as vasopressin, an astringent, blood plasma, a blood product (such as platelets, prothrombin, thrombin, fibrin, fibrinogen, thromboplastin or a clotting factor), an enzyme, an enzyme inhibitor; a tissue growth stimulant or a healing promoter including nitric oxide, nitric oxide generating agent, gelatin, collagen, whole blood, blood plasma, a blood product (such as platelets, prothrombin, thrombin, fibrin, fibrinogen, thromboplastin or a clotting factor), angiogenin, angiopoietin-1, a diacylglycerol, del-1, follistatin, an interleukin, a leptin, midkine, pleiotrophin, progranulin, proliferin, a transforming growth factor, a granulocyte colony-stimulating factor, a hepatocyte growth factor, a scatter factor, an epidermal growth factor, a nerve growth factor, a fibroblast growth factor, a keratinocyte growth factor, a placental growth factor, an endothelial cell growth factor, a platelet-derived growth factor, a tumor necrosis factor, vascular endothelial growth factor (VEGF), a vascular permeability factor, insulin-like growth factor, a hormone, hydroxyapatite, demineralized bone, natural bone, a bone product, a bone morphogenetic protein, a chondrocyte, a calcium phosphate derivative, an enzyme, an enzyme inhibitor, a stem cell, thrombin inhibitor, pepsin; an anti-infective agent including nitric oxide, a nitric oxide generating agent, tea tree oil, peroxide, an antibiotic such as ampicillin, a fatty acid, an antifungal, an antiviral, an immunogenic agent; an adhesive agent including a crosslinkable substrate, a crosslinking agent, natural polymer, a synthetic polymer, a cellulosic polymer, a carboxymethylcellulose, a polyethylene glycol or a PEG derivative, a polybutylene terephthalate or PBT derivative, a polyethylene oxide or PEO derivative, a polyacrylic acid, a poly methyl vinyl ether/maleic anhydride copolymer, a poly methyl vinyl ether/maleic acid copolymer, a poly vinyl methyl-ether maleate, a poly ethylene oxide, a cationic polyacrylamide polymer, an alginic acid derivative, chitosan, a glucosamine such as n-acetylglucosamine, a natural or synthetic protein, gluten, gelatin, collagen, ampicillin, a gum, karaya gum, a cellulosic gum, a phospholipids, a fatty acid, bentonite, fumed silica, colloidal silica, micronized silica, diatomaceous earth, talc, titanium dioxide; a swelling agent including a natural or synthetic swellable polymer, karaya gum, a cellulosic gum, an alginic acid derivative, gelatin, chitosan, polyacrylic acid, a polyacrylic acid derivative including a crosslinked polyacrylic acid, a glucosamine such as n-acetylglucosamine; a viscosity enhancer; including a crosslinkable substrate, a crosslinking agent, a natural polymer, a synthetic polymer, a cellulosic polymer, carboxymethylcellulose, a polyethylene glycol or PEG derivative, a polybutylene terephthalate or PBT derivative, a polyethylene oxide or PEO derivative, a poly methyl vinyl ether/maleic anhydride copolymer, a poly methyl vinyl ether/maleic acid copolymer, a poly vinyl methyl-ether maleate, a poly ethylene oxide, a cationic polyacrylamide polymer, am alginic acid derivative, chitosan, a glucosamine such as n-acetylglucosamine, a natural or synthetic protein or peptide (such as gluten, collagen hydrolysates, gelatin or collagen), a gum, karaya gum, ampicillin, a cellulosic gum, a phospholipid, a fatty acid, a multiparticulate (such as a polylactic-co-glycolide or PLGA multiparticulate, bentonite, fumed silica, colloidal silica, micronized silica, diatomaceous earth, talc or titanium dioxide), an oleaginous ointment base, an absorbent ointment base, an emulsion ointment base;

an anesthetic including clove oil, eugenol, tea tree oil, benzocaine, lidocaine, dibucaine, pramoxine, dyclonine; a solvent or co-solvent; including dodecane, peroxide, phospholipids, a fatty acid, polyethylene glycol, a PEG derivative, polyethylene oxide, a PEO derivative, a polybutylene terephthalate, a PBT derivative, a biological fluid; a thinning agent including a natural or synthetic polymer, a polar or nonpolar solvent (such as ethanol, dodecane, polyethylene glycol or a PEG derivative), a phospholipid, a fatty acid, an exothermic compound (such as calcium bromide, calcium oxide or calcium chloride); a filler including a hyaluronic acid, a fatty acid, polyethylene glycol, a PEG derivative, polyethylene oxide, a PEO derivative, collagen, a biological fluid, a blood product; an anti-oxidant including hydrophilic and lipophilic antioxidants (such as ascorbic acid, ascorbic acid salts and esters, butylated hydroxyanisole, butylated hydroxytoluene, lecithin, isopropyl palmitate, isopropyl myristate, ubiquinol, phenolics, tocopherols, retinols, calciferols, thioglycolic acid, sulfur dioxide, cysteine hydrochloride, sulfites, ascorbic palmitates or alkyl gallates); an anti-scarring or anti-inflammatory therapeutic including an onion extract, a UV radiation blocker, a steroid, a non-steroidal anti-inflammatory drug, an oleaginous ointment base, an absorbent ointment base, an emulsion ointment base, an enzyme, an enzyme inhibitor, a tissue growth inhibitor (such as certain antibiotics, chemotherapeutics and irritants); a physiologically compatible monovalent ion, divalent ion, trivalent ion or salt thereof (such as a calcium derivative, a potassium derivative, a sulfate derivative, a chloride derivative, a fluoride derivative, potassium aluminum sulfate, aluminum chloride, ammonium chloride, ferric sulfate, ferric sub-sulfate or copper sulfate); a bleaching agent including a teeth whitening substance, a peroxide; a miscellaneous therapeutic including nitric oxide, nitric oxide generating agent, botulinum toxin; a controlled-release component or composition including a multiparticulate, a multiparticulate containing a therapeutic, a poly(lactic-co-glycolide) (PLGA) multiparticulate, a polyanhydride multiparticulate; an embolism promoting material including a multiparticulate, a multiparticulate containing a therapeutic, a poly(lactic-co-glycolide) (PLGA) multiparticulate, a polyanhydride multiparticulate, a polyvinyl alcohol multiparticulate; or any combination thereof.

Moreover, in any disclosed formulation, the augmentative agent or therapeutic may be suspended in the formulation, dissolved in the formulation or a combination thereof. The controlled-release component or composition may be a biodegradable release controlling agent, a biodegradable release controlling agent or composition containing a therapeutic in the form of a multiparticulate, a biodegradable polymer containing a therapeutic in the form of a multiparticulate or a combination thereof.

In addition, any disclosed formulation may be a liquid, gel or semisolid, it may form a liquid crystalline phase prior to or after application, and the liquid-crystal forming compound may be hydrophobic and/or amphiphilic, and any disclosed formulation is preferably biocompatible and/or biodegradable.

Other embodiments provide a method for effectively controlling biological fluid at a desired site of a subject, the method comprising administering an effective amount of a therapeutic formulation at the site comprising about 25% to 100% by weight liquid-crystal forming compound and about 0% to about 75% by weight solvent for a period of time effective to control biological fluid at the desired site. In a related embodiment, there is provided a method for effectively controlling biological fluid at a desired site of a subject, the method comprising administering an effective amount of any formulation as disclosed above, for a period of time effective to control biological fluid at the desired site. In such embodiments, the methods may further effectively control biological fluid by promoting hemostasis at the desired site; promoting coagulation at the desired site; facilitating healing by inducing local effects at the desired site; and/or maintaining moisture at the desired site, particularly when desired site is a burn.

Still another embodiment provides a method for effectively controlling biological fluid at a desired site of a subject by providing any formulation as disclosed above, the formulation comprising tissue filler and having increased residence time at or near the desired site, such that the formulation resists bodily clearance. In related embodiments, providing increased residence time further comprises administering a liquid-crystal formulation, thereby lessening migration within and surrounding the desired site so as to increase residence time at the site. In such methods, the tissue filler may be a dermal filler, bone filler, brain filler, synovial filler or muscle filler; the dermal filler may be used for lip augmentation or to adjust the apparent tonicity of skin or attenuate the appearance of wrinkles; the synovial filler may be used as a synovial fluid replacement media; and the tissue filler may be injected via needle access to site.

Yet another embodiment provides a method for effectively controlling biological fluid at a desired site of a subject by providing any formulation as disclosed above wherein effectively controlling biological fluid further comprises forming a protective barrier to effect sealing of tissues at the desired site, so as to control flow and exchange of biological fluid and promote sealing of tissue via formation of the protective barrier at the site. In related embodiments, the formulation may provide a healing matrix for tissue re-growth; the tissue may be an epithelial, connective, skeletal, glandular, muscular or nervous tissue site of the subject; and the desired site may be bone tissue, dural tissue, vascular tissue, spinal tissue, or hepatic tissue.

Another particular embodiment provides a method for effectively controlling biological fluid at a desired site in a subject by providing any formulation as disclosed above, wherein effectively controlling biological fluid further comprises retarding the formation of a surgical adhesion, so as to inhibit the formation of undesired scar tissue that may result in the post operative period at or adjacent to a site of surgical intervention. In related embodiments, retarding the formation of a surgical adhesion further comprises administering the formulation such that it coats internal tissue and impedes intimate contact and exchange of bodily fluid containing physiological stimulants for scarring at the site, thereby retarding development of any surgical tissue adhesion. In more particular embodiments, the formulation forms a liquid crystal system, thereby lessening migration within or upon bodily tissues and attenuating clearance of the formulation from the site of application via the high viscosity and form fitting shape of the formed liquid crystal system; administering may further comprise administering a formulation containing a scar tissue growth inhibitor to further retard the formation of an internal surgical scar tissue adhesion; and the scar tissue growth inhibitor may be an antineoplastic agent, an anti-inflammatory agent, an antibiotic agent or a combination thereof.

In still other related embodiments, the surgical field or site may be treated with the formulation by spray coating, hot-melt coating, direct transfer, manual application or a combination thereof; the bodily fluid may be any of biological fluid, blood, urine, saliva, serous fluid, synovial fluid, gastric secretions, cerebrospinal fluid, sweat, tears, bile, vitreous humor, chyme, mucous, lymph or wound exudates; and the desired site may be part of the female gynecological region, including the vagina, uterus or cervix.

In any of the disclosed methods for effectively controlling biological fluid at a desired site of a subject, effectively controlling biological fluid may further comprise inducing local effects at the desired site so as to facilitate healing; administering a formulation containing an augmentative agent, therapeutic agent, or a combination thereof; the site may be an acute trauma wound or a chronic wound wherein the acute trauma wound may be an abrasion, a burn, a laceration, a puncture or an incision and wherein the chronic wound may be a leg, decubitus, fungal, diabetic, gastric, foot, sacral or indolent ulcer.

In related embodiments, effectively controlling may further comprise delivering the formulation to the large intestinal, rectal or anal cavity by application of an ointment, gel, enema or suppository; filling a tissue void including those created by trauma or a surgical procedure; administering the formulation in a molten state; administering the formulation by continuous or intermittent positive-pressure administration; and/or administering the formulation to the site by laparoscopy, irrigation, continuous spray, intermittent spray, continuous stream, intermittent stream, lavage, douche, enema, implant, deposition, direct manual administration or by incorporation into a medical article. The embodiments are not limited to any specific routes or methods of administration, and therefore include intravenous, intramuscular, subcutaneous, nasal, ocular, sublingual, buccal, oral, dermal, vaginal, surgical deposition or rectal administration. In embodiments administering the formulation by incorporation into a medical article, the medical article may be a wound dressing, a sponge, an article for the nose, an adhesive bandage, a wound packing, an internal vascular closure packing, an external vascular closure dressing, a swellable absorbent article, a fibrotic wound packing or a feminine hygiene article. In related embodiments, administering may further comprise administering by douche, suppository, enema, irrigation, spray, stream, manual application, lavage, or impregnation of a medical article, wherein direct manual administration may be by direct transfer by hand or by an instrument controlled by the hand and wherein indirect manual application may be by utilizing a carrier for or a device impregnated with the formulation, to aid transfer of the formulation to the site, wherein transfer comprises manually wiping, smearing or holding the formulation onto and/or into a tissue site.

In another particular embodiment, there is provided a method for controlling blood loss at a site of a subject, the method comprising administering a thrombin inhibitor formulation as disclosed above at a site of blood loss of a subject, wherein the formulation facilitates blood coagulation, thereby controlling blood loss at the site. In related embodiments, the blood loss is any of menstrual discharge, postpartum bleeding, reproductive tract bleeding or is any bodily blood or exudate discharge containing water and the blood loss may be internal or external. In such embodiments, administering may further comprise filling a tissue void, including those created by trauma, disease or a surgical procedure; administering by continuous or intermittent positive-pressure administration; administering the formulation in a molten state; or administering to the site by laparoscopy, irrigation, continuous spray, intermittent spray, continuous stream, intermittent stream, lavage, douche, enema, implant, deposition, direct manual application or by incorporation into a medical article. In particular related embodiments, the medical article may be any of a wound dressing, a sponge, an article for the nose, an adhesive bandage, a wound packing, an internal vascular closure packing, an external vascular closure dressing, a swellable absorbent article, a fibrotic wound packing or a feminine hygiene article.

Still other particular embodiments provide a method for administering any therapeutic formulation as described above, the method comprising administering the formulation directly to a venous or arterial tissue at a vascular access site of a subject; administering the formulation so as to contact tissue adjacent to a vascular access site of a subject; administering by back-filling an access tract with the formulation from the vascular access site to the epidermis; delivering the formulation to superficial tissue of a venous or arterial access site; and/or utilizing an implant article for administering which has been impregnated with the formulation. In such embodiments, the article may comprise collagen, gelatin, chitosan, chitin, poly(lactic-co-glycolide) (PLGA), poly n-acetylglucosamine or a combination thereof; and administering may further comprise application of the therapeutic formulation during or immediately upon withdrawal of a needle, sheath or access catheter from the access site.

Another particular embodiment provides a method for administering any therapeutic formulation as described above to a desired tissue site of a subject, the method comprising administering the formulation to the desired tissue site to effect tissue sealing, wherein the tissue is selected from the group consisting of epithelial, connective, skeletal, glandular, muscular and neural tissue. In related embodiments, administering may further comprises administering to neural tissue to inhibit progression of paralysis, wherein the formulation comprises cerebrospinal fluid as a solvent, and wherein the cerebrospinal fluid is obtained from the subject. Other related embodiments may further comprise administering the formulation to a bone tissue site to plug and seal an opening, thereby inhibiting loss of bodily fluid and providing a protective barrier at the opening, wherein the formulation comprises whole blood, platelets, platelet-rich plasma, or plasma as a solvent, wherein the whole blood or platelets, platelet-rich plasma, or plasma is obtained from the subject, and wherein administering further comprises promoting bone re-growth.

In more particular related embodiments, there is provided a method for administering any therapeutic formulation as described above to a desired tissue site of a subject to effect tissue sealing, wherein effecting tissue sealing may further comprise filling a tissue void, including those created by trauma or a surgical procedure; administering may further comprise continuous or intermittent positive-pressure administration; administering the formulation in a molten state; and/or administering to the site by laparoscopy, irrigation, continuous spray, intermittent spray, continuous stream, intermittent stream, lavage, douche, enema, implant, deposition, direct manual applications or by incorporation into a medical article. In such embodiments, the medical article may be any of a wound dressing, a sponge, an article for the nose, an adhesive bandage, a wound packing, an internal vascular closure packing, an external vascular closure dressing, a swellable absorbent article, a fibrotic wound packing or a feminine hygiene article.

Still another particular embodiment provides a method for facilitating effective closure of a vascular wound or incision site at a desired site of a subject, the method comprising administering, optionally by positive pressure, an effective amount of a biocompatible biodegradable therapeutic formulation at the vascular wound site or incision site, the formulation comprising about 25% to 100% by weight liquid-crystal forming compound and about 0% to about 75% by weight solvent, wherein the formulation effects hemostasis by physically staunching blood flow, absorbs fluid, and induces local effects at the site within about 10 minutes or less of administration at the site, thereby facilitating effective closure of the vascular wound or incision. In related particular embodiments, the formulation physically staunches blood flow, absorbs fluids, and induces local effects within about 5 minutes or less, more particularly within about 1 minute or less, and still more particularly within about 30 seconds or less.

Yet another particular embodiment provides a method for delivering any formulation as described above to a desired site of a subject, the method comprising delivering the formulation to the desired site by injection, more particularly, administering the formulation by injection directly within the circulatory system of the subject, still more particularly injecting via an access device such as a wire guided catheter, and still more particularly injecting and thereby delivering the formulation for embolization therapy. In such embodiments, the embolization therapy is treatment of tumors, or treatment of bleeding.

Another particular embodiment provides a method for inhibiting tissue adhesion to a medical article, the method comprising coating said medical article with any formulation as described above, thereby inhibiting tissue adhesion to said article and reducing pain and trauma upon application and subsequent removal of the medical article. In particular related embodiments, the medical article is a wound dressing, a burn dressing, fibrotic packing, an adhesive bandage, a hemostatic article for nose-bleeds, an implantable medical article or medical hardware intended for a human or veterinary subject.

Still another particular embodiment provides a method for sterilizing any formulation described above or device containing such formulation, the method comprising sterile filtering, distillation, thermally exposing, exposing to ionizing radiation, aseptically processing, heating with steam under pressure, heating with pressure, or exposing to a gas the formulation or device containing the formulation prior to use.

Another particular embodiment provides an emergency hemostasis kit for effecting hemostasis at a site of bleeding in a subject within about 15 minutes or less, the kit comprising any sterile formulation as described above, and means for applying the formulation to the site of bleeding. In a more particular related embodiment, the means for applying the formulation is any of a positive pressure irrigation device, a swab, a spray applicator, a syringe, an eye dropper, a wound dressing, an adhesive bandage, a squeeze bulb, a pipette, an enema, a suppository, a sealed container for direct application to the site of bleeding after unsealing, or any other suitable means for applying said formulation.

In other related embodiments, kits may be prepared for other methods of treatment, such as methods for controlling bodily fluid, promoting healing, treating a burn, dressing a wound, sealing tissue, as disclosed above, said kits providing appropriate sterile formulations and means for applying such formulations. Related embodiments may further comprise wound dressing articles, such as bandages, gauze, plugs, sutures, cleaning materials, all treated with or containing sterile formulations for the required treatment, the kits being assembled in easy to use containers.

Another particular embodiment provides a method for effectively mimicking soft bodily tissues at a desired site in a subject, the method comprising administering an effective amount of a cosmetic medical formulation as disclosed above internally at the desired site. In related embodiments, the formulation is any of a liquid, a gel or a semi-solid; the formulation may be adapted for use as a fill media for a cosmetic medical and reconstructive implant device; the formulation may form a viscous phase after filling the device; the formulation may form a viscous phase prior to filling the device. In other related embodiments, the implant device is a breast implant, a tissue void implant, a gluteal implant, a facial implant or a pectoris implant; the formulation fill media may be increased, decreased or exchanged via an access site to the implant when the implant is positioned just under the skin of a subject; the implant device may be constructed of a plurality of compartments to hold media wherein the compartments allow media movement between compartments and wherein compartments are connected by an opening, the size of which affects rate of media movement between compartments; the implant device is constructed of a plurality of compartments to hold media wherein the compartments do not allow media movement between compartments; or the plurality of compartments have a wedge shape, each compartment expanding from a center point where the compartments meet centrally, as in a pie-graph.

BRIEF DESCRIPTION OF THE DRAWINGS

The foregoing features of the invention will be more readily understood by reference to the following detailed description, taken with reference to the accompanying drawings, in which:

FIGS. 4A and 4B show a hemostatic agent according to the present invention being applied to a rat tail amputation site resulting in immediate post-irrigation hemostasis (A) and total control of bleeding (B).

FIGS. 5A and 5B show application of a hemostatic agent according to the present invention to a rat saphenous vein laceration (A) followed by post-irrigation hemostasis and control of bleeding (B).

FIGS. 6A and 6B show application by pulse pressure stream of a hemostatic agent according to the present invention seconds after an exsanguinating injury (on 50% and 25% excision of rat liver lobes) to a swine liver lobe (A) followed by immediate post-irrigation hemostasis and total control of bleeding.

FIGS. 7A and 7B show application of a hemostatic agent using a non-optimal pouring technique according to the present invention seconds after a 10-minute exsanguinating injury (2 cm incision) to a swine liver (A) followed by immediate post-irrigation hemostasis and control of bleeding, despite the poor technique application (B).

FIGS. 8A and 8B show pulse pressure stream application of a hemostatic agent according to the present invention seconds after an exsanguinating injury to a swine liver lobe (A), compared to application of a hemostatic agent according to the present invention seconds after an exsanguinating injury to a swine liver lobe using non-optimal pouring (B).

FIGS. 9A and 9B show application of a hemostatic agent using a positive pulse-pressure stream technique according to the present invention at a 5-minute exsanguinating injury (3 cm incision) to a swine liver lobe (A) followed by post-irrigation hemostasis, hemorrhage control using gauze treated with a hemostatic formulation according to the present invention, and clean immediate control of bleeding (B).

DETAILED DESCRIPTION OF SPECIFIC EMBODIMENTS

Definitions

Figure 1:
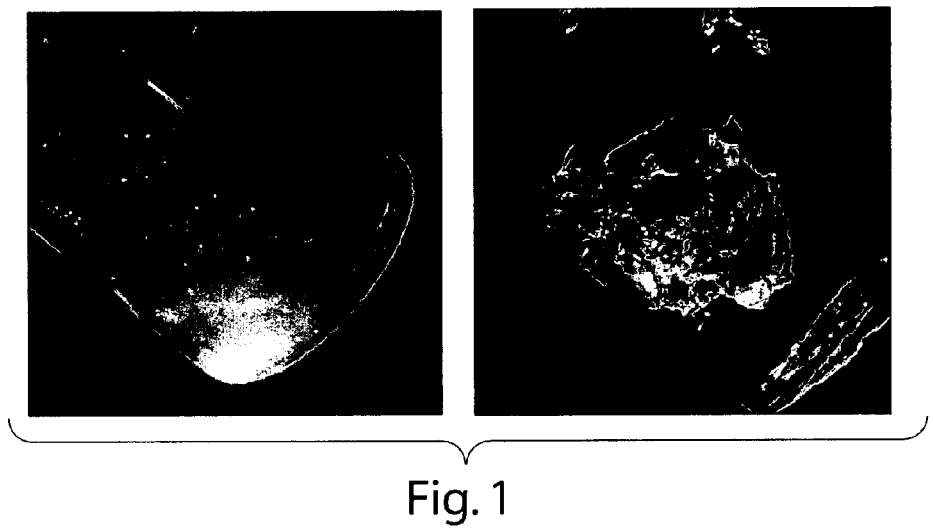
FIG. 1 is a photograph showing three physical states of a hemostatic composition in accordance with the present invention, wherein the physical state is a liquid, a more viscous liquid or a firm semi-solid, respectively, from left to right.
Figure 2A:
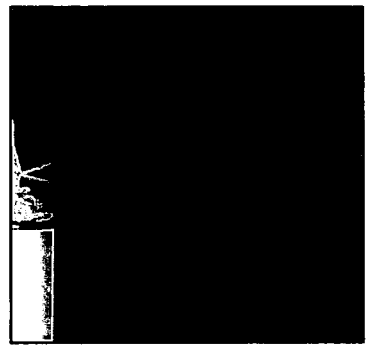
FIGS. 2A, 2B and 2C show a series of photographs representing a hemostatic composition in accordance with the present invention as a low-viscosity liquid that can be sprayed, a viscous gel that can be extruded from a syringe, or a firm semi-solid, respectively, from left to right.
Figure 2B:
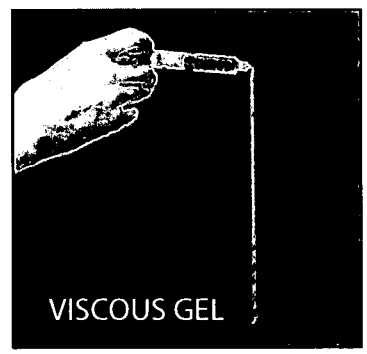
Figure 2C:
Figure 3A:
FIGS. 3A and 3B show a prior art hemostatic agent being applied to a rat tail amputation site (A) and failure to control bleeding (B).
Figure 3B:
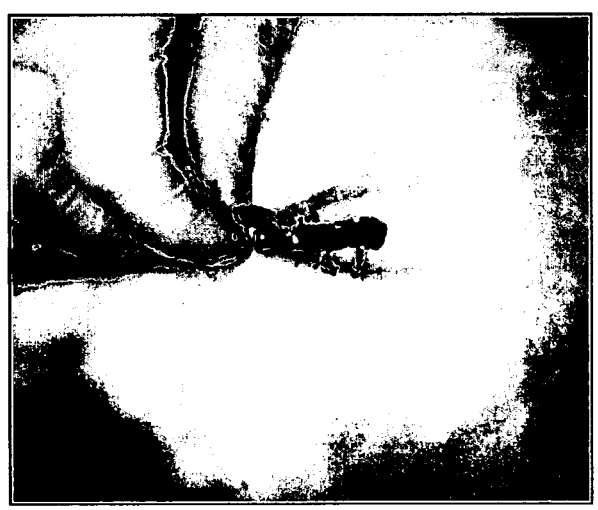
Figure 10A:
FIGS. 10A through E show application of a hemostatic agent according to the present invention applied to a dog bite on a human thumb (A) followed by post-irrigation hemostasis and control of bleeding (B), continued hemostasis after 12 hrs (C) and minimal tissue disfigurement and scarring at site of injury (D and E).
Figure 10B:
Figure 10C:
Figure 10D:
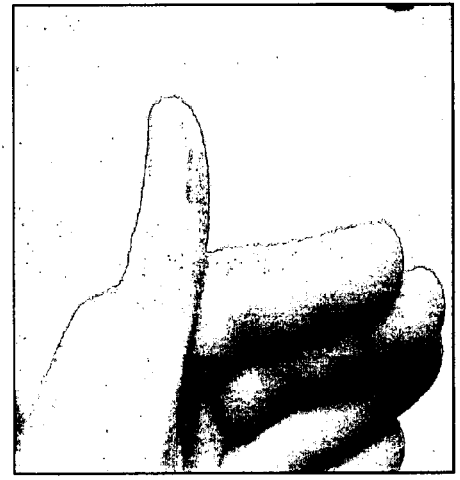
Figure 10E:
Figure 11A:
FIGS. 11A through D show Scanning Electron Microscope (SEM) images at 2 seconds (A), 1 minute (B), 5 minutes (C) and 10 minutes (D) after application of a hemostatic agent according to the present invention to a site of bleeding in a subject. As can be seen in (A), platelets have already lined up non-randomly at the site at two seconds, large numbers of platelets have congregated at the site by one minute (B), evidence of tertiary clotting/healing is evident after 5 minutes (C), and continued clotting/healing is evident at 10 minutes after application (D).
Figure 11B:
Figure 11C:
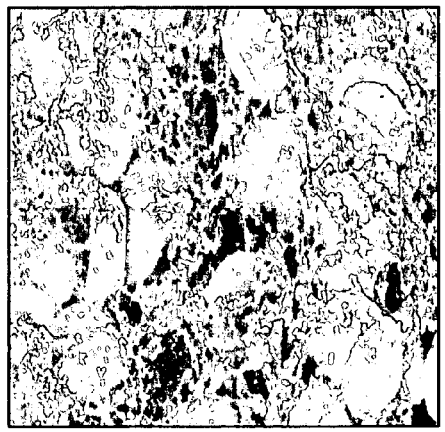
Figure 11D:
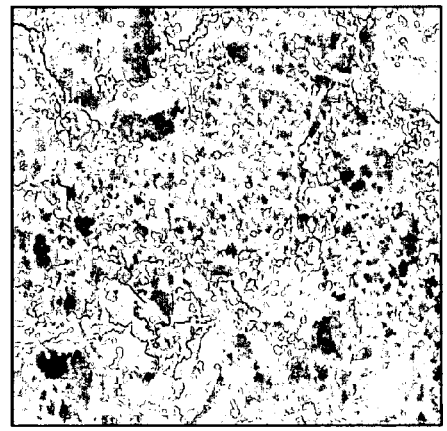
Figure 12A:
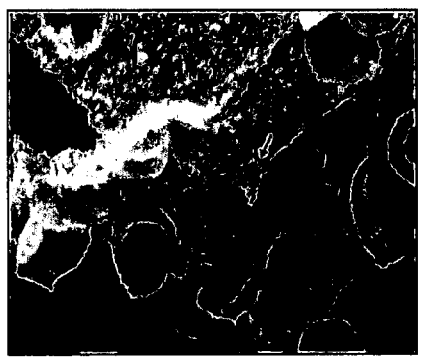
FIGS. 12A and 12B show a hemostatic formulation according to the present invention comprising glyceryl monooleate and whole blood in the cubic liquid crystalline phase, wherein distorted whole red blood cells can be seen binding to the liquid crystal GMO formulation, as well as an activated platelet and a thin mesh of fibrin at 20 seconds (A) and a close-up of an activated platelet binding to the formulation (B).
Figure 12B:
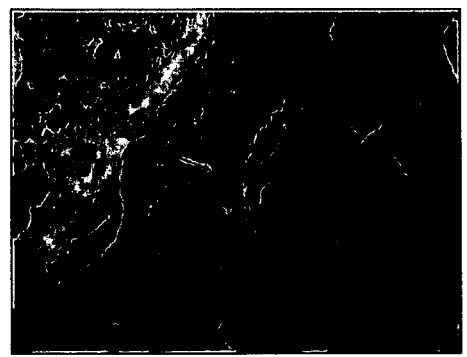

As used in this description and the accompanying claims, the following terms shall have the meanings indicated, unless the context otherwise requires:

"Liquid crystal" as broadly defined and used herein, means any substance that exhibits a phase of matter that has properties between those of a conventional liquid, and those of a solid crystal. By example, a liquid crystal may flow like a liquid, but have the molecules in the liquid arranged and oriented in a crystal-like way. The phases can be distinguished and verified by optical properties and other methods. Viewed in a microscope under polarized light illumination, a liquid crystal material will appear to have a distinct texture. Therefore, "Liquid-crystal forming compounds" as defined herein are any substances that have self assembling properties and may exhibit a liquid crystalline state. Liquid-crystal forming compounds are typically moderate size organic molecules, but they can also be large (i.e. some polymers) which tend to be elongated and oblong-shaped, although a variety of other shapes are possible as well. Because of their elongated shape, under appropriate conditions the molecules can exhibit orientational order, such that all the axes line up in a particular direction. In consequence, the bulk order has profound influences on the physicochemical properties of the material, and the way the material acts. For example, if the direction of the orientation varies in space, the orientation of light (i.e., the polarization) can follow this variation. A well-known application of this phenomenon is the ubiquitous liquid crystal display. Under other conditions the molecules may form a stack of layers along one direction, but remain liquid like (in terms of the absence of translational order) within the layers. As the system changes from one of these phases to another, a variety of physical parameters such as susceptibility and heat capacity, will exhibit "pretransitional behavior." Based solely on symmetry, this behavior may be related to other physical systems, such as superconductivity, magnetism, or superfluidity; this is the so-called "universality" of these phase transitions. As used herein, "Liquid crystal" also encompasses a large class of highly anisometric molecules (as opposed to ordinary fluids that are isotropic in nature and appear optically, magnetically, electrically, etc. to be the same from any perspective) which result in anisotropic macroscopic behavior, giving rise to unusual, fascinating, and potentially technologically and biologically relevant behavior. Examples of such molecules include certain polymers and materials of biological significance, such as fatty acids, fatty acid esters, proteins, peptides, carbohydrates, glycolipids and lipids. As used herein, a disclosed formulation comprising a liquid crystal-forming compound may be a liquid, gel or semisolid, it may form a liquid crystalline state or phase, including derivations of, but not limited to, a micelle phase, a lamellar phase, a cubic phase, a hexagonal phase, a sponge phase, a smectic phase, a nematic phase or mixtures thereof, prior to administration, during administration or acquired in situ after administration. The liquid crystal-forming compound may be hydrophobic and/or amphiphilic. When highly viscous or semisolid liquid crystalline phases are desirable, fatty acid esters such as monoglycerides are preferred, unless the viscosity of the formulation is augmented by the addition of a viscosity enhancer as disclosed herein. Moreover, the disclosed formulations comprising a liquid crystal-forming compound are preferably biocompatible and/or biodegradable.

"Glyceryl monooleate" as used herein, encompasses glycerol monooleate, the two being used interchangeably to represent the same monoester formed between the reaction of oleic acid with glycerol. Accordingly, as used herein, "GMO" stands for glyceryl monooleate or glycerol monooleate, the two being understood to be one and the same compound. For all formulations, the exact percentage of the liquid crystal-forming compound, particularly fatty acid esters of polyols such as glyceryl monooleate and also phospholipids such as lecithin may vary, depending on the source or supplier of the compound, because all commercially available reagents are not identical, and exact purity levels may vary. For example, one commercial source for GMO lists the purity as not less than 80% glyceryl monooleate.

"Positive Pressure" as used herein, means use of force to create pressure greater than would exist by existing atmospheric, gravitational or a biological systemic force alone, whether through irrigation, continuous spray, intermittent spray, continuous stream, intermittent stream, lavage, douche, enema, direct manual application or through physical pressure applied manually, directly or indirectly, or the application of force through manual or automated use of a device. The phrase, used in conjunction with application, as in "Positive Pressure Application" includes application of a formulation as disclosed herein, or a device comprising a formulation as disclosed herein, by using a positive pressure irrigation device such as a swab, a spray applicator, a stream applicator, a single syringe, a dual syringe, an eye dropper, a wound dressing, an adhesive bandage, a squeeze bulb, a pipette, an enema, a suppository, a sealed container for direct application to the site of bleeding after unsealing, or any other suitable means for applying the formulation in conjunction with the use of indirect or direct force. For example, in a wound to a vein or artery, where blood loss is exacerbated by pumping from the heart, positive pressure means use of force at the site to apply a disclosed formulation, or device comprised such formulation, to an extent greater than the force from the heart contributing to the blood loss. Other examples of positive pressure include using force generated by spray or pulsed stream application of a disclosed formulation to a desired site, such as an acute wound, such that the formulation is at least momentarily directed, using a force greater than gravity, to the desired site.

"Controlling biological fluids" as used herein, means broadly the modulation of biological fluid equilibrium and flow as it relates to the biological site reference. Such modulation includes at least the partial limitation of fluid loss, the maintenance of critical fluids and the preservation of fluid physiological balance where gradients are relevant.

"Biological fluids" as used herein, means broadly any fluid contained within or excreted from a human or animal including blood, urine, saliva, serous fluid, synovial fluid, gastric secretions, cerebrospinal fluid, sweat, tears, bile, chyme, mucous, vitreous humor, lymph, wound exudate or combinations thereof.

"Therapeutic agent" and "Therapeutic" when used herein mean having or exhibiting the ability to heal, treat or provide other benefits, including a substance or composition having or exhibiting the ability to heal, treat or generally provide a benefit. As used herein, "Therapeutic agent" and "Therapeutic" encompasses "Augmentative agent" and "Augmentative", meaning having or exhibiting the ability to enhance or provide a desired attribute or attributes to or of a system thereby impacting the performance of the system for the intended use.

"Polar solvent" when used herein means a solvent, co-solvent or combination of solvents that possesses an electric dipole. Examples include water, any aqueous liquid including biological fluids that contain polar substances such as blood, urine, saliva, serous fluid, synovial fluid, gastric secretions, cerebrospinal fluid, sweat, tears, bile, chyme, mucous, vitreous humor, lymph or wound exudate, various alkanols, polyethylene glycol, propylene glycol, polypropylene glycol, glycol, glycerin, isotonic aqueous solution, physiologic buffered systems or combinations thereof.

"Non-Polar solvent" when used herein means a solvent, co-solvent or combination of solvents that does not possess a significant electric dipole. These solvents are particularly useful as co-solvents, phase modifiers and for providing fluidity to the liquid-crystal forming compounds. Examples include alkanes, plant derived oils such as cotton seed oil, certain highly esterified glycerides such as certain triglycerides or combinations thereof.

"Surgical" as broadly used herein includes any tissue invasive procedure such as cutting, abrading, suturing, laser or otherwise physically changing body tissues regardless of the profession of any individual performing such procedures. For example, surgical as defined herein includes dental extractions by dentists and vascular interventions by interventional radiologist.

"Hemostatic" when used herein as an adjective, means broadly having or exhibiting the ability to significantly limit or arrest the flow of blood under the conditions referenced or apparent when the word is used. When used as a noun herein, or as the noun derivative "hemostat", the nouns mean any substance or composition having or exhibiting the ability to significantly limit or arrest the flow of blood. The noun derivative "hemostasis" as used herein, means having blood flow in the state of significantly limited flow or arrest. The definitions herein are intended as broad descriptors and are not limited to any specific mechanism of blood coagulation or other means of blood flow limitation or arrest.

One particular embodiment of the invention provides a method of producing a liquid crystalline formulation capable of being formulated in fluid or non-fluid forms of varying viscosity wherein the forms may be applied to the site of injury or tissue disruption in humans or animals to slow or stop the loss of blood or bodily fluids. The method may comprise producing the liquid crystalline formulation by hydrating or solvating a liquid crystalline precursor material, for example, glyceryl monooleate (GMO). The liquid crystalline formulation of glyceryl monooleate is produced by heating the material to melting with the addition of an aqueous solvent system. A particular example of an aqueous solvent system appropriate for addition to the crystalline precursor material is sodium chloride solution (saline solution). An example of a liquid crystalline formulation formulated as a fluid or in a liquid state is a GMO-based formulation comprising about 5% normal saline w/w (final NaCl concentration about 0.045%, by weight), therein producing a formulation with a viscosity in the range of about 80-300 centipoise. An example of a liquid crystalline formulation being formulated as a fluid semisolid would be a GMO-based formulation comprising about 10% saline, therein producing a formulation with a viscosity in the range of about 1000-5000 centipoise. A further example of a liquid crystalline formulation being formulated as a non-fluid formulation would be a GMO-based formulation comprising about 30% saline; therein producing a formulation with a viscosity in excess of about 1,200,000 centipoise. An example of a method of application includes pressurized irrigation as achieved through a syringe or other similar device.

Another embodiment of the invention is a method of producing a liquid crystalline formulation capable of being formulated in fluid or non-fluid forms of varying viscosity that may be applied to the sight of injury or tissue disruption in humans or animals to slow or stop the loss of blood or bodily fluids, the method comprising: producing the liquid crystalline formulation by hydrating or solvating the liquid crystalline precursor material. An example of a liquid crystalline precursor material is glyceryl monooleate (GMO). The liquid crystalline formulation of glyceryl monooleate is produced by heating the material to melting with the addition of a non-aqueous solvent formulation. An example of a non-aqueous solvent system is isopropyl myristate. An example of a liquid crystalline formulation being formulated as a fluid or liquid state would be a GMO-based formulation containing about 10% isopropyl myristate producing a formulation with a viscosity in about the range of 80-500 centipoise.

Another embodiment of the invention is a method of producing a liquid crystalline formulation capable of being formulated in fluid or non-fluid forms of varying viscosity that may be applied to the sight of injury or tissue disruption in humans or animals to slow or stop the loss of blood or bodily fluids, the method comprising: producing the liquid crystalline formulation by hydrating or solvating the liquid crystalline precursor material. An example of a liquid crystalline precursor material is glyceryl monooleate (GMO). The liquid crystalline formulation of glyceryl monooleate is produced by heating the material to melting with the addition of a non-aqueous, semi-polar solvent system. An example of a non-aqueous, semipolar solvent system is Polyethylene Glycol 200. An example of a liquid crystalline formulation being formulated as a fluid or liquid state would be a GMO-based formulation containing about 10% Propylene Glycol producing a formulation with a viscosity in about the range of 80-500 centipoise.

Another embodiment of the invention is a method of producing a liquid crystalline formulation capable of being formulated in fluid or non-fluid forms of varying viscosity that may be applied to the sight of injury or tissue disruption in humans or animals to slow or stop the loss of blood or bodily fluids, the method comprising: producing the liquid crystalline formulation by hydrating or solvating the liquid crystalline precursor material. An example of a liquid crystalline precursor material is glyceryl monooleate (GMO). The liquid crystalline formulation of glyceryl monooleate is produced by heating the material to melting with the addition of a mixture of aqueous and non-aqueous solvent system. An example of a liquid crystalline formulation being formulated as a fluid or liquid state would be a GMO-based formulation containing about 5% normal saline and about 5% ethanol producing a formulation with a viscosity in about the range of 80-500 centipoise.

(Method of Producing LCS Containing Augmentative/Therapeutic Agent)

Another embodiment provides a pharmaceutical formulation comprising a liquid-crystal forming compound and optionally an augmentative or therapeutic agent that may be applied to the sight of injury or tissue disruption in humans or animals to slow or stop the loss of blood or bodily fluids. More particularly, the formulation comprises a solvated or hydrated liquid crystalline formulation optionally including an augmentative agent, therapeutic agent, or a combination thereof, dissolved, suspended or dispersed in an aqueous solvent system prior to production of the liquid crystalline formulation. An example of an aqueous solvent system is purified water. An example of an augmentative or therapeutic agent is a soluble calcium salt such as calcium gluconate or calcium chloride.

Another embodiment provides a method of producing a liquid crystalline formulation optionally containing an augmentative/therapeutic agent that may be applied to the sight of injury or tissue disruption in humans or animals to slow or stop the loss of blood or bodily fluids, the formulation comprising a solvated or hydrated liquid crystalline formulation, optionally with a therapeutic agent or agents suspended or dispersed in an aqueous solvent system prior to production of the liquid crystalline formulation. An example of an aqueous solvent system is purified water. An example of a therapeutic agent is colloidal silicon dioxide.

Another embodiment provides a method of producing a liquid crystalline formulation optionally containing a therapeutic agent that may be applied to the sight of injury or tissue disruption in humans or animals to slow or stop the loss of blood or bodily fluids, the formulation comprising a solvated or hydrated liquid crystalline formulation, optionally with a therapeutic agent or agents dissolved or dispersed in a non-aqueous solvent system prior to production of the liquid crystalline formulation. An example of a non-aqueous solvent system is ethanol. An example of a therapeutic agent is benzocaine.

Another embodiment provides a method of producing a liquid crystalline formulation optionally containing a therapeutic agent that may be applied to the sight of injury or tissue disruption in humans or animals to slow or stop the loss of blood or bodily fluids, the formulation comprising a solvated or hydrated liquid crystalline formulation, optionally with a therapeutic agent or agents suspended, dissolved or dispersed in a non-aqueous solvent system prior to production of the liquid crystalline formulation. An example of a non-aqueous solvent system is cottonseed oil. An example of a therapeutic agent is aluminum potassium sulfate.

Another embodiment provides a method of producing a liquid crystalline formulation optionally containing an augmentative/therapeutic agent that may be applied to the sight of injury or tissue disruption in humans or animals to slow or stop the loss of blood or bodily fluids, the formulation comprising a solvated or hydrated liquid crystalline formulation with a augmentative/therapeutic agent or agents dissolved or dispersed in a liquid crystalline precursor material prior to production of the liquid crystalline formulation. An example of an augmentative/therapeutic agent is phosphatidylserine.

Another embodiment provides a method of producing a liquid crystalline formulation optionally containing an augmentative/therapeutic agent that may be applied to the sight of injury or tissue disruption in humans or animals to slow or stop the loss of blood or bodily fluids, the comprising a solvated or hydrated liquid crystalline formulation, optionally with an augmentative/therapeutic agent or agents suspended or dispersed in a liquid crystalline precursor material prior to production of the liquid crystalline formulation. An example of an augmentative/therapeutic agent is collagen.

(Method of Application/Delivery of LCS)

Another embodiment of the invention provides an improved method of delivery to a sight of injury or tissue disruption reducing the possibility of secondary contamination. The improved method of delivery comprising: gravity directed stream or flow of the formulation by means of the primary packaging container. (Terminally sterile)

Another embodiment of the invention provides an improved method of delivery to a sight of injury or tissue disruption reducing the possibility of secondary contamination. The improved method of delivery comprising: directed pressurized spray or stream of the formulation by means of mechanical pressurization as in a plunger or piston type system.

Another embodiment of the invention provides an improved method of delivery to a sight of injury or tissue disruption reducing the possibility of secondary contamination. The improved method of delivery comprising: directed pressurized spray or stream of the formulation by means of mechanical pressurization as in a squeeze-container type system.

Another embodiment of the invention provides an improved method of delivery to a sight of injury or tissue disruption reducing the possibility of secondary contamination. The improved method of delivery comprising: directed pressurized spray or stream of the formulation by means of gaseous propellants as in an aerosol type system.

(Method of Application/Delivery of LCS within or Upon Secondary Medical Structures)

Another embodiment of the invention provides a method of delivery to a sight of injury or tissue disruption. The method of delivery comprising: delivery of the formulation through conveyance within or upon a medical structure such as a surgical gauze.

Another embodiment of the invention provides a method of delivery to a sight of injury or tissue disruption. The method of delivery comprising: delivery of the formulation through conveyance within or upon a medical structure such as a cotton swab device.

Another embodiment of the invention provides a method of delivery to a sight of injury or tissue disruption. The method of delivery comprising: delivery of the formulation through conveyance within or upon a medical structure such as a primary occlusive or non-occlusive bandage.

(Method of Application/Delivery of LCS—Vascular Closure)

Another embodiment of the invention provides a method of delivery to the tissues surrounding the site of venous or arterial access. The method of delivery comprising: delivery of the formulation by direct injection or instillation into the access tract upon withdrawal of a needle or access catheter.

Another embodiment of the invention provides a method of delivery to the tissues surrounding the site of venous or arterial access. The method of delivery comprising: delivery of the formulation by injection or instillation through a multiple lumen, balloon catheter system used to back-fill the access tract. The catheter system is withdrawn following placement of the invention.

Another embodiment of the invention provides a method of delivery to the superficial tissues of a venous or arterial access site. The method of delivery comprising: delivery of the formulation by direct application to the superficial access tract during or immediately upon withdrawal of a needle or access catheter. The invention may be placed on the sight alone or in combination with an occlusive or non-occlusive dressing or pressure dressing.

(Method of Application/Delivery of LCS—Embolization Therapy)

Another embodiment of the invention provides a method of delivery to the circulatory system for embolization therapy. The method of delivery comprising: delivery of the formulation by injection through an intravenous or intra-arterial access method such as a wire-guided catheter.

(Method of Application/Delivery of LCS—Feminine Hygiene)

Another embodiment of the invention provides a method of delivery to the feminine reproductive tract. The method of delivery comprising: delivery of the formulation through conveyance within or upon catamenial products within or upon the feminine reproductive tract such as a tampon or feminine napkin or pad.

Another embodiment of the invention provides a method of delivery to the feminine reproductive tract. The method of delivery comprising: delivery of the formulation through conveyance in the form of a douche.

Another embodiment of the invention provides a method of delivery to the feminine reproductive tract. The method of delivery comprising: delivery of the formulation through conveyance in the form of a suppository or ovule.

(Method of Application/Delivery of LCS—Lower GI-Rectal)

Another embodiment of the invention provides a method of delivery to the large intestine, rectal and anal structures. The method of delivery comprising: delivery of the formulation through conveyance in the form of a enema.

Another embodiment of the invention provides a method of delivery to the large intestine, rectal and anal structures. The method of delivery comprising: delivery of the formulation through conveyance in the form of a suppository.

Another embodiment of the invention provides a method of delivery to the large intestine, rectal and anal structures. The method of delivery comprising: delivery of the formulation through conveyance in the form of a semisolid ointment.

(Lubricant)

Another embodiment of the invention provides a method of persistent lubrication to assist in the placement or removal a device or structure within the body. The method comprising: application of the formulation within or upon a device or structure such as a surgical epistaxis gauze or nasal packing. The liquid crystalline formulation provides a physical, insoluble barrier between the tissue and the device or structure that will easily sheer and lubricate the surfaces for insertion or removal from the site of application.

(Cosmetic Surgery)

Another embodiment of the invention provides a method of utility for direct cosmetic augmentation of tissues. The method comprising: injection of the formulation into tissues of the body to augment the volume of the tissues to increase the aesthetic features.

Another embodiment of the invention provides a method of utility in implantable cosmetic augmentation devices such as breast and gluteal implants. The method comprising: producing the formulation having the consistency of the desired adipose or muscle tissue and subsequent incorporation into a polymeric or elastomeric envelope for implantation.

(Biohardware)

Another embodiment of the invention provides a method of application to implantable prosthetic hardware to reduce or eliminate the formation of bacterial biofilm infections. The method comprising: application of the formulation within or upon a hardware device or structure by a method of spray coating, hot-melt coating or dip coating prior to or at the time of implantation. The liquid crystalline formulation provides a physical, insoluble barrier that resists the adhesion or deposition of bacteria capable of producing biofilm infections.

(Wound Healing)

Another embodiment of the invention provides a method of application to chronic wounds of soft tissues such as decubitus ulcers. The method comprising: application of the formulation to the wound bed following cleaning or debridement. The liquid crystalline formulation provides a physical, insoluble barrier that resists contamination as well as maintains an advantageous moisture balance beneath the barrier.

(Reduction/Elimination of Surgical Adhesions)

Another embodiment of the invention provides a method to reduce or eliminate the formation of surgical adhesions. The method comprises applying the formulation near or upon the site of a surgical manipulation. The liquid crystalline formulation provides a physical, insoluble barrier between the manipulated tissues reducing the propensity for hypertrophic scarring leading to tissue adhesion.

Example 1

| | |
|---|---|
| Purified Water, USP | 5% |
| Glyceryl monooleate | 95% |

Purified water, USP was heated to approximately 40° C. Glyceryl Monooleate (GMO) was heated to melting. The purified water was combined with GMO. The resulting system was well mixed and allowed to return to ambient temperature undisturbed. The resulting mixture produced a hazy liquid formulation with a viscosity in the approximate range of 80-500 centipoise.

The present example possessed characteristics making it operable as a hemostatic, fluid-controlling, tissue sealant and/or wound healing formulation for delivery by means of lavage or irrigation, as well as by pressurized methods of delivery, to superficial or internal wounds, and affected tissue. The formulation may also be used in wound dressing articles for treating burns of varying degree, to protect the burn surface from exposure to microorganisms thereby inhibiting infection, control fluid (oozing) and protect the burn surface from abrasion and new injury/loss of tissue upon change of dressing.

Example 2

| Normal Saline for Injection, USP | 5% |
|---|---|
| Glyceryl monooleate | 95% |

Normal Saline for Injection, USP, was heated to approximately 40° C. Glyceryl Monooleate (GMO) was heated to melting. The Normal Saline was combined with GMO. The resulting system was well mixed and allowed to return to ambient temperature undisturbed. The resulting mixture produced a hazy liquid formulation with a viscosity in the approximate range of 80-500 centipoise.

The present example possessed characteristics making it operable as a hemostatic, fluid-controlling, tissue sealant and/or wound healing formulation for delivery by means of lavage or irrigation, as well as by pressurized methods of delivery, to superficial or internal wounds, and affected tissue. The formulation may also be used in wound dressing articles for treating burns of varying degree, to protect the burn surface from exposure to microorganisms thereby inhibiting infection, control fluid (oozing) and protect the burn surface from abrasion and new injury/loss of tissue upon change of dressing.

Example 3

| Ethanol, 190 proof | 5% |
|---|---|
| Glyceryl monooleate | 95% |

Ethanol 95% was heated to approximately 40° C. in a closed container. Glyceryl Monooleate (GMO) was heated to melting. The ethanol was combined with GMO. The resulting system was well mixed and allowed to return to ambient temperature undisturbed. The resulting mixture produced a hazy liquid formulation with a viscosity in the approximate range of 80-500 centipoise.

The present example possessed characteristics making it operable as a hemostatic, fluid-controlling, tissue sealant and/or wound healing formulation for delivery by means of lavage or irrigation, as well as by pressurized methods of delivery, to superficial or internal wounds, and affected tissue. The formulation may also be used in wound dressing articles for treating burns of varying degree, to protect the burn surface from exposure to microorganisms thereby inhibiting infection, control fluid (oozing) and protect the burn surface from abrasion and new injury/loss of tissue upon change of dressing.

Example 4A

| Ethanol, 190 proof | 5% |
|---|---|
| Normal Saline for Injection, USP | 5% |
| Glyceryl monooleate | 90% |

Example 4B

| Ethanol, USP | 2% |
|---|---|
| Normal Saline for Injection, USP | 6% |
| Monoerucin | 92% |

In both examples, ethanol and normal saline was mixed thoroughly and heated to approximately 40° C. in separate closed containers. Glyceryl Monooleate (GMO) and Monoerucin were heated to melting in separate containers. The corresponding ethanol/normal saline mixtures were combined with GMO and Monoerucin respectively. The resulting systems were well mixed and allowed to return to ambient temperature undisturbed. The resulting mixtures produced hazy liquid formulations with a viscosity in the approximate range of 80-500 centipoise.

The present examples possessed characteristics making them operable as hemostatic, fluid-controlling, tissue sealant and/or wound healing formulations for delivery by means of lavage or irrigation or by pressurized methods of delivery, to superficial or internal wounds, and affected tissue. The formulations may also be used in wound dressing articles for treating burns of varying degree, to protect the burn surface from exposure to microorganisms thereby inhibiting infection, control fluid (oozing) and protect the burn surface from abrasion and new injury/loss of tissue upon change of dressing.

Example 5

| Propylene Glycol, USP | 5% |
|---|---|
| Glyceryl monooleate | 95% |

Propylene Glycol, USP, was heated to approximately 40° C. Glyceryl Monooleate (GMO) was heated to melting. The propylene glycol was combined with GMO. The resulting system was well mixed and allowed to return to ambient temperature undisturbed. The resulting mixture produced a clear liquid formulation with a viscosity in the approximate range of 80-200 centipoise.

The present example possessed characteristics making it operable as a hemostatic, fluid-controlling, tissue sealant and/or wound healing formulation for delivery by means of lavage or irrigation, as well as by pressurized methods of delivery, to superficial or internal wounds, and affected tissue. The formulation may also be used in wound dressing articles for treating burns of varying degree, to protect the burn surface from exposure to microorganisms thereby inhibiting infection, control fluid (oozing) and protect the burn surface from abrasion and new injury/loss of tissue upon change of dressing.

Example 6

| | |
|---|---|
| Cottonseed Oil, NF | 20% |
| Glyceryl monooleate | 80% |

Cottonseed Oil, NF, was heated to approximately 40° C. Glyceryl Monooleate (GMO) was heated to melting. The cottonseed oil was combined with GMO. The resulting system was well mixed and allowed to return to ambient temperature undisturbed. The resulting mixture produced a clear liquid formulation with a viscosity in the approximate range of 80-200 centipoise.

The present example possessed characteristics making it operable as a hemostatic, fluid-controlling, and/or wound healing formulation for delivery by means of lavage or irrigation, as well as by pressurized methods of delivery, to superficial or internal wounds, and affected tissue. The formulation may also be used in wound dressing articles for treating burns of varying degree, to protect the burn surface from exposure to microorganisms thereby inhibiting infection, control fluid (oozing) and protect the burn surface from abrasion and new injury/loss of tissue upon change of dressing. The use of the nonpolar solvent in the present example offered the ability to alter the rate of conversion to the final liquid crystalline state as well as the character of the system. In this instance the rate of conversion was slowed to a process that required 2-5 minutes for completion with a reduction in the viscosity of the terminal state.

Example 7

| | |
|---|---|
| Phosphatidylserine 20% powder | 10% |
| Normal Saline for Injection, USP | 5% |
| Glyceryl monooleate | 85% |

Phosphatidylserine 20% (PS) powder was dispersed in and hydrated with Normal Saline for Injection, USP. Glyceryl Monooleate (GMO) was heated to melting. The PS mixture was combined with GMO and mixed well. The resulting mixture produced a brownish-yellow gel formulation with a viscosity in the approximate range of 800-2000 centipoise.

The present example possessed characteristics making it operable as a hemostatic formulation for delivery by means of lavage or irrigation, as well as by pressurized methods of delivery, to superficial or internal wounds and affected tissue in instances where precision of application and reduction in potential migration of the system in the field or to surrounding tissues is desired. The addition of phosphatidylserine serves an adjunctive role as a potential mediator in the normal coagulation cascade.

Example 8

| | |
|---|---|
| Phosphatidylserine 20% powder | 10% |
| Normal Saline for Injection, USP | 5% |
| Glyceryl monooleate | 85% |

Glyceryl Monooleate (GMO) was heated to melting. Phosphatidylserine 20% (PS) powder was dispersed in the molten GMO. The molten mixture was then hydrated with Normal Saline for Injection, USP, with mixing. The PS mixture was combined with GMO and mixed well. The resulting mixture produced a brownish-yellow liquid formulation with a viscosity in the approximate range of 60-200 centipoise.

The present example possessed characteristics making it operable as a hemostatic formulation and tissue sealant for delivery by means of lavage or irrigation, as well as by pressurized methods of delivery, to superficial or internal wounds and affected tissue. The addition of phosphatidylserine serves an adjunctive role as a potential mediator in the normal coagulation cascade.

Example 9

| | |
|---|---|
| Ampicillin 250 mg Powder for Injection | |
| Glyceryl monooleate | qs 1 ml |

Glyceryl Monooleate (GMO) was heated to melting. Ampicillin 250 mg powder for reconstitution was dispersed in the molten GMO. The resulting mixture produced a high viscosity and yet a pliable mass.

The present example produced a pliable formulation operable as a therapeutic dressing system for insertion into and upon wound beds as produced by venous stasis and diabetic foot ulcers. The formulation facilitates healing and may be used to prevent or treat secondary bacterial infections that often accompany these conditions. The formulation may also be used in wound dressing articles for treating burns of varying degree, to control infection, control fluid (oozing) and protect the burn surface from abrasion and new injury/loss of tissue upon change of dressing.

Example 10

| | |
|---|---|
| Potassium Chloride Solution 1 meq/mL | 10% |
| Glyceryl monooleate | 90% |

Concentrated potassium chloride (KCl) 2 meq/ml was diluted to a concentration of 1 meq/ml using Water for Injection, USP. This dilution was heated to approximately 40° C. Glyceryl Monooleate (GMO) was heated to melting. The KCl solution was combined with GMO and mixed well. The resulting mixture produced a clear solid formulation with a viscosity in the approximate range in excess of 1.2 million centipoise.

Example 11

| | |
|---|---|
| Potassium Chloride Solution 1 meq/mL | 5% |
| Glyceryl monooleate | 95% |

Potassium Chloride (KCl) 2 meq/ml was diluted to a concentration of 1 meq/ml using Water for Injection, USP. This dilution was heated to approximately 40° C. Glyceryl Monooleate (GMO) was heated to melting. The KCl solution was combined with GMO and mixed well. The resulting mixture produced a hazy liquid formulation with a viscosity in the approximate range of 80-200 centipoise.

The present example possessed characteristics making it operable as a hemostatic formulation for delivery by means of lavage or irrigation, as well as by pressurized methods of delivery, to superficial or internal wounds and affected tissue.

Example 12

| | |
|---|---|
| Cholesterol, USP | 10% |
| Normal Saline for Injection, USP | 5% |
| Glyceryl monooleate | 85% |

Glyceryl Monooleate (GMO) was heated to melting. Cholesterol, USP powder was dispersed in the molten GMO. The molten mixture was then hydrated with Normal Saline for Injection, USP with mixing. The resulting mixture produced a white liquid formulation with a viscosity in the approximate range of 60-200 centipoise.

The present example possessed characteristics making it operable as a hemostatic or as a wound formulation for delivery by means of lavage or irrigation, as well as by pressurized methods of delivery, to superficial or internal wounds and affected tissue. The addition of cholesterol serves to slow the rate of conversion to as well as the consistency of the terminal phase.

Example 13

| | |
|---|---|
| Crospovidone, NF | 10% |
| Normal Saline for Injection, USP | 5% |
| Glyceryl monooleate | 85% |

Glyceryl Monooleate (GMO) was heated to melting. Crospovidone, NF powder was dispersed in the molten GMO. The molten mixture was then hydrated with Normal Saline for Injection, USP with mixing. The resulting mixture produced a firm, white gel formulation with a viscosity in the approximate range of 10,000-30,000 centipoise.

The present example possessed characteristics making it operable as a hemostatic formulation for delivery by means of lavage or irrigation, as well as by pressurized methods of delivery, to superficial or internal wounds and affected tissue, in instances where precision of application and reduction in potential migration of the system in the field or to surrounding tissues is desired. The addition of crospovidone serves an adjunctive role as a swelling agent that is able to absorb blood or bodily fluids and subsequently swell in a controllable fashion to further apply secondary physical pressure to the treated area.

Example 14

| | |
|---|---|
| Crospovidone, NF | 10% |
| Normal Saline for Injection, USP | 5% |
| Glyceryl monooleate | 85% |

Glyceryl Monooleate (GMO) was heated to melting. Povidone K29/32, NF powder was dispersed in the molten GMO. The molten mixture was then hydrated with Normal Saline for Injection, USP with mixing. The resulting mixture produced a thick, opaque, silky gel formulation with a viscosity in the approximate range of 2000-5000 centipoise.

The present example possessed characteristics making it operable as a hemostatic or therapeutic wound care formulation for delivery to superficial or internal wounds and affected tissue by means of lavage or irrigation, as well as by pressurized methods of delivery, in instances where precision of application and reduction in potential migration of the agent in the field or to surrounding tissues is desired. The formulation may also be used in wound dressing articles for treating burns of varying degree, to protect the burn surface from exposure to microorganisms thereby inhibiting infection, control fluid (oozing) and protect the burn surface from abrasion and new injury/loss of tissue upon change of dressing. The addition of crospovidone serves to increase the residence time and inhibit migration from the tissue.

Example 15

| | |
|---|---|
| Pemulen ® TR2 | 1% |
| Normal Saline for Injection, USP | 5% |
| Glyceryl monooleate | 85% |

Glyceryl Monooleate (GMO) was heated to melting. Pemulen® TR2, NF powder was dispersed in the molten GMO. The molten mixture was then hydrated with Normal Saline for Injection, USP with mixing. The resulting mixture produced a pliable gel formulation with a viscosity in the approximate range of 100,000-300,000 centipoise. It is understood that other methacrylic acid copolymers and derivatives thereof may be interchanged for Pemulen® TR2 in the present example. The present example possessed characteristics making it operable as a hemostatic or therapeutic wound care formulation for delivery to superficial or internal wounds and affected tissue by means of lavage or irrigation, as well as by pressurized methods of delivery, in instances where precision of application and reduction in potential migration of the agent in the field or to surrounding tissues is desired.

Example 16

| | |
|---|---|
| Polyethylene Glycol (PEG) 400, NF | 10% |
| Polyethylene Glycol (PEG) 200, NF | 5% |
| Glyceryl monooleate | 85% |

PEG 400, NF and PEG 200, NF were mixed and heated to approximately 40° C. Glyceryl Monooleate (GMO) was heated to melting. The PEG mixture was combined with GMO. The resulting system was well mixed and allowed to return to ambient temperature undisturbed. The resulting mixture produced a clear liquid formulation with a viscosity in the approximate range of 80-200 centipoise. In the present embodiment, other MW PEGs may be useful as well and interchanged with those described above to produce alternative formulations having similar properties making such formulations operable for hemostatic applications.

The present example possessed characteristics making it operable as a hemostatic, fluid-controlling, and/or wound healing formulation for delivery by means of lavage or irrigation, as well as by pressurized methods of delivery, to superficial or internal wounds, and affected tissue. The formulation may also be used in wound dressing articles for treating burns of varying degree, to protect the burn surface from exposure to microorganisms thereby inhibiting infection, control fluid (oozing) and protect the burn surface from abrasion and new injury/loss of tissue upon change of dressing.

Example 17

| | |
|---|---|
| Isopropyl Myristate, NF | 5% |
| Glyceryl monooleate | 95% |

Isopropyl Myristate, NF, (IPM) was heated to approximately 40° C. Glyceryl Monooleate (GMO) was heated to melting. The IPM was combined with GMO. The resulting system was well mixed and allowed to return to ambient temperature undisturbed. The resulting mixture produced a hazy gel formulation with a viscosity in the approximate range of 800-3000 centipoise.

The present example possessed characteristics making it operable as a hemostatic formulation for delivery by means of lavage or irrigation, as well as by pressurized methods of delivery, to superficial or internal wounds and affected tissue, in instances where precision of application and reduction in potential migration of the system in the field or to surrounding tissues is desired.

Example 18

| | |
|---|---|
| Calcium Gluconate 10% Solution | 5% |
| Glyceryl monooleate | 95% |

Calcium Gluconate solution was heated to approximately 40° C. Glyceryl Monooleate (GMO) was heated to melting. The Calcium Gluconate was combined with GMO. The resulting system was well mixed and allowed to return to ambient temperature undisturbed. The resulting mixture produced a hazy liquid formulation with a viscosity in the approximate range of 80-200 centipoise.

The present example possessed characteristics making it operable as a hemostatic formulation for delivery by means of lavage or irrigation, as well as by pressurized methods of delivery, to superficial or internal wounds and affected tissue. The addition of calcium ions served an adjunctive role as a physiologic mediator to supplement the normal coagulation cascade.

Example 19

| | |
|---|---|
| Sodium Hyaluronate | 2.5% |
| Normal Saline for Injection, USP | 5% |
| Glyceryl monooleate | 92.5% |

The Sodium Hyaluronate was dissolved in the Normal Saline and heated to approximately 35° C. Glyceryl Monooleate (GMO) was heated to melting. The Sodium Hyaluronate solution was combined with GMO. The resulting system was well mixed and allowed to return to ambient temperature undisturbed. The resulting mixture produced a hazy liquid formulation with a viscosity in the approximate range of 1000-3000 centipoise.

The present example possessed characteristics making it operable as a hemostatic formulation for delivery by means of lavage or irrigation, as well as by pressurized methods of delivery, to superficial or internal wounds and affected tissue in instances where precision of application and reduction in potential migration of the system in the field or to surrounding tissues is desired. The formulation may also be used in wound dressing articles for treating burns of varying degree, to protect the burn surface from exposure to microorganisms thereby inhibiting infection, control fluid (oozing) and protect the burn surface from abrasion and new injury/loss of tissue upon change of dressing. The addition of hyaluronate serves as a adjuvant to assist in the physiologic process of healing.

Example 20

| | |
|---|---|
| Sodium Hyaluronate | 2.5% |
| Normal Saline for Injection, USP | 5% |
| Glyceryl monooleate | 92.5% |

Glyceryl Monooleate (GMO) was heated to melting. The Sodium Hyaluronate was dispersed with agitation in the GMO. The Normal Saline solution was combined with GMO mixture. The resulting system was well mixed and allowed to return to ambient temperature undisturbed. The resulting mixture produced a hazy liquid formulation with a viscosity in the approximate range of 1000-3000 centipoise.

The present example possessed characteristics making it operable as a hemostatic formulation for delivery by means of lavage or irrigation, as well as by pressurized methods of delivery, to superficial or internal wounds and affected tissue, in instances where precision of application and reduction in potential migration of the system in the field or to surrounding tissues is desired. The formulation may also be used in wound dressing articles for treating burns of varying degree, to protect the burn surface from exposure to microorganisms thereby inhibiting infection, control fluid (oozing) and protect the burn surface from abrasion and new injury/loss of tissue upon change of dressing. The addition of hyaluronate serves as a adjuvant to assist in the physiologic process of healing.

Example 21

| | |
|---|---|
| Hydrogenated Lecithin | 5% |
| Normal Saline for Injection, USP | 5% |
| Glyceryl monooleate | 90% |

The Hydrogenated Lecithin was dispersed in the Normal Saline and heated to approximately 40° C. Glyceryl Monooleate (GMO) was heated to melting. The Hydrogenated Lecithin solution was combined with GMO. The resulting system was well mixed and allowed to return to ambient temperature undisturbed. The resulting mixture produced a hazy liquid formulation with a viscosity in the approximate range of 50,000-100,000 centipoise.

The present example possessed characteristics making it operable as a hemostatic formulation for delivery by means of lavage or irrigation, as well as by pressurized methods of delivery, to superficial or internal wounds and affected tissue, in instances where precision of application and reduction in potential migration of the system in the field or to surrounding tissues is desired. The addition of lecithin serves as a source of physiologic phospholipids intermediates to accentuate the normal host coagulation cascade.

Example 22

| | |
|---|---|
| Hydrogenated Lecithin | 5% |
| Normal Saline for Injection, USP | 5% |
| Glyceryl monooleate | 90% |

Glyceryl Monooleate (GMO) was heated to melting. The Hydrogenated Lecithin was dispersed with agitation in the GMO. The Normal Saline solution was combined with GMO mixture. The resulting system was well mixed and allowed to return to ambient temperature undisturbed. The resulting mixture produced a hazy liquid formulation with a viscosity in the approximate range of 1000-3000 centipoise.

The present example possessed characteristics making it operable as a hemostatic formulation for delivery by means of lavage or irrigation, as well as by pressurized methods of delivery, to superficial or internal wounds and affected tissue, in instances where precision of application and reduction in potential migration of the system in the field or to surrounding tissues is desired. The addition of lecithin serves as a source of physiologic phospholipids intermediates to accentuate the normal host coagulation cascade.

Example 23

| | |
|---|---|
| Propylene Glycol, USP | 5% |
| Water for Injection, USP | 2.5% |
| Ethanol, USP | 2.5% |
| Glyceryl monooleate | 90% |

Glyceryl Monooleate (GMO) was heated to melting. The Propylene Glycol, Water for Injection and Ethanol were combined and mixed well forming a homogeneous solution. The molten GMO and PG/Water/Ethanol solution were combined with vigorous mixing. The resulting system was allowed to return to ambient temperature undisturbed. The resulting mixture produced a clear to hazy liquid formulation with a viscosity in the approximate range of 80-200 centipoise.

The present formulation is well suited for hemostatic applications by low and high pressure delivery methods. Following manufacture, the formulation was placed into a compressed air aerosol system. The formulation is easily applied at rates ranging from a fine mist to a course spray. This method of delivery allows for convenient and uniform application over a large surface area. The present example possesses characteristics making it particularly operable as a fluid-controlling, and/or wound healing formulation for use in direct spray-application to burns, or in wound dressing articles for treating burns of varying degree, to protect the burn surface from exposure to microorganisms thereby inhibiting infection, control fluid (oozing) and protect the burn surface from abrasion and new injury/loss of tissue upon change of dressing. This formulation was also effective in a rabbit model for embolic therapy either as describe or with multiparticulate PLGA microspheres suspended therein.

Example 24

| | |
|---|---|
| Propylene Glycol, USP | 2.56% |
| Water for Injection, USP | 5.1% |
| Glyceryl monooleate | 92.3% |

Glyceryl Monooleate (GMO) was heated to melting. The Propylene Glycol and Water for Injection were combined and mixed well forming a homogeneous solution. The molten GMO and PG/Water solution were combined with vigorous mixing. The resulting system was allowed to return to ambient temperature undisturbed. The resulting mixture produced a clear to hazy liquid formulation with a viscosity in the approximate range of 3000-5000 centipoise.

The present formulation is well suited for hemostatic applications by low and high pressure delivery methods. Following manufacture, the formulation was placed into a pump-type spray bottle. The formulation is easily applied as a thin stream and a course spray. This method of delivery allows for convenient and directed application to a specific tissue surface area. The present example possesses characteristics making it particularly operable as a fluid-controlling, and/or wound healing formulation for use in direct spray-application to burns, or in wound dressing articles for treating burns of varying degree, to protect the burn surface from exposure to microorganisms thereby inhibiting infection, control fluid (oozing) and protect the burn surface from abrasion and new injury/loss of tissue upon change of dressing.

Example 25

| | |
|---|---|
| Thrombin | 1000 U/g |
| Normal Saline for Injection, USP | 5% |
| Glyceryl monooleate | 95% |

Normal Saline for Injection, USP, was heated to approximately 40° C. Glyceryl Monooleate (GMO) was heated to melting. The Normal Saline was combined with GMO. The resulting system was well mixed and allowed to return to ambient temperature undisturbed. The thrombin was dispersed in the system with gentle mixing. The resulting mixture produced a hazy liquid formulation with a viscosity in the approximate range of 80-500 centipoise. The present example possessed a lower viscosity making it operable as a hemostatic formulation for delivery by means of lavage or irrigation as well as by pressurized methods of delivery to superficial or internal wounds and affected. The addition of thrombin served an adjunctive role as a physiologic mediator to supplement the normal coagulation cascade.

Example 26A

| | |
|---|---|
| Plasma, platelets, platelet-rich plasma, or whole blood | ~1 to ~45% by weight |
| Glyceryl monooleate | ~35 to ~99% by weight |

Example 26B

| Plasma, platelets, platelet-rich plasma, or whole blood | ~6% by weight |
|---|---|
| Glyceryl monooleate | ~94% by weight |

Disease-free, drug-free, platelets, platelet-rich plasma, plasma or whole blood, from a patient to be treated, or other acceptable blood donor source, is heated to approximately 40° C. Glyceryl Monooleate (GMO) is heated to melting. The platelets, platelet-rich plasma, plasma or whole blood is then combined with GMO. The resulting system is well mixed and allowed to return to ambient temperature undisturbed. The resulting mixture produces a liquid formulation with a relatively low viscosity. Both formulations proved effective to seal bone tissue as presently described as well as after the addition of excess aqueous liquids including biological fluids to make a high viscosity semisolid to smear seal open bone.

The present example possesses characteristics making it operable as a hemostatic, fluid-controlling, and/or wound healing formulation for delivery by means of lavage or irrigation, as well as by pressurized methods of delivery, to superficial or internal wounds, and affected tissue.

It is envisioned that many if not most of the other formulations specified above in Examples 1-25 may be formulated with donor-grade platelets, platelet-rich plasma, plasma or whole blood, either in place of the described solvent, or in addition to, to create formulations suitable for a variety of hemostatic, fluid-controlling and/or wound-healing purposes.

Example 27

An Absorbent Article

In an embodiment there is provided an absorbent layer comprising a liquid-impermeable and moisture vapor-permeable outer layer having an inner surface and an outer surface, the inner surface essentially coextensive with an outer surface of the absorbent layer. The liquid-permeable liner may have a surface that is substantially coextensive with an inner surface of the absorbent layer such that the absorbent layer is located between the liquid-permeable sheet and the outer layer. In addition, the article has a biocompatible biodegradable hydrophobic composition on at least a portion of a surface of the liquid-permeable liner opposite that which is coextensive with the inner surface of the outer layer, wherein the composition comprises from about 50% to 99% by weight liquid-crystal forming compound and about 0% to 50% by weight solvent. When the absorbent device is used as a wound dressing, it can be positioned over the wound with the absorbent layer positioned adjacent to the wound. The device may then be adhered to the skin around the wound, for example, by tape or an adhesive wrap.

In another embodiment, the absorbent layer and the outer layer are not substantially coextensive and the other layer extends beyond at least a portion of the outer perimeter of the absorbent layer to form an extended portion with an upper and lower surface. The lower surface of the extended portion is adjacent to the absorbent layer and at least a portion of the lower surface carries an adhesive layer which can be used to adhere the absorbent article to the skin around a wound. Optionally, this embodiment can further comprise a release liner that is substantially coextensive with the outer layer and adhered to the liquid-permeable liner by the adhesive layer. The release liner would then be removed from the absorbent article prior to application to the wound or site of application of the article.

The liquid permeable layer permits passage of a liquid, e.g. exudate, from the wound or site of treatment into the absorbent layer, and preferably prevents adherences of the absorbent layer to the site of application of the article. Aqueous media absorbent devices frequently will comprise a substantially aqueous media impervious and moisture vapor-permeable outer layer, which may comprise any suitable material, such as polyethylene, polypropylene and polyurethane, with a thickness of about 0.02 mm to help retain fluid within the absorbent material. The outer layer may also comprise a fabric treated with a water repellent material. The outer layer may also be a moisture vapor-permeable adhesive coated film such as is described in U.S. Pat. No. 4,726,989.

The liquid-permeable layer may comprise any material, such as polyester, polyolefin, rayon, and the like, that is substantially porous and permits aqueous media to readily pass through into the underlying absorbent core. Examples of suitable adhesives for the adhesive layer include any of the non-cytotoxic adhesives such as hot-melt spray adhesives including HL-1685-X or HL-1710-X, both of which are commercially available from H. B. Fuller Co., St. Paul, Minn. The hot melt adhesive can be applied using spiral spray adhesive systems such as those commercially available from Nordson Corporation, Duluth, Ga. Typical adhesive application rates using such systems are about 6 to 10 grams/m$^2$. The absorbent layer may comprise fibers combined with commonly used materials to prepare absorbent fabrics or batts, such as wood pulp, cellulose, cotton, rayon, recycled cellulose, shredded cellulose sponge and binders, or shredded keratin. Typically the thickness of the absorbent layer is from about 0.5 to 10 mm. Release liner may be of any polymeric film, paper or foil known in the art to be useful as a release liner. Examples of useful liners include 50 g/m2 basis weight SC 501FM40 white Sopal Flexible Packaging available from Day Cedex, France.

Embodiments as described may be bandages, gauze dressings, sponge dressings, or any other absorbent article, with added adhesive or simply the or article alone, prepared under sterile conditions and pre-packed in sterile packages for direct usage at a wound or other desired site.

Example 28

Hemostasis of Liver Lacerations in a Murine Model

Animal #1—an adult rodent was anesthetized, and then the tail was completely lacerated to produce a robust arterial bleed into 37° C. saline. After two minutes without slowing or cessation, tail was removed from saline and one drop of Formulation #2 was applied. Bleeding stopped, the after ~1 min, slow oozing started. This secondary bleeding was completely stopped with the second application.

Animal #2—Tail bleed was induced as in animal #1. After 10 sec in 37° C. saline the robustly bleeding tail was removed from saline and coated with a drop of Formulation #2. This greatly slowed the bleed with some breakthrough from arterial pressure. A second and third drop of Formulation #2 largely, but did not completely control, the bleed. A transverse laparotomy was performed to expose abdominal cavity. In the process of exposing the liver, a bleed occurred from an unintended wound of a major vessel (unidentified). The bleeding from this wound was completely controlled with two drops of Formulation #2.

Animal #3—After establishing a plane of anesthesia and performing transverse laparotomy, the liver was lacerated and allowed to freely bleed onto gaze for 30 seconds, at which time the surface of the laceration and surrounding field was liberally filled with Formulation #2. Bleeding was promptly controlled. Gauze with excess Formulation #2 was removed after one minute, and then a second piece of gauze was placed under the lacerated organ. Minimal blood was deposited from the wound site on the second piece of gauze. A tail bleed was induced as with animal #1, and then completely controlled with two drops of Formulation #2.

Overall conclusions concerning in vivo bleeding experiments—Formulation #2 application successfully controlled bleeding from capillaries and small vessels. Major arterial bleeds might require a GMO-impregnated matrix for mechanical strength.

Example 29

Hemostasis of Liver Lacerations in a Murine Model

Eight male Sprague-Dawley rats (400-450 g) were anesthetized using ketamine 90 mg/kg and xylazine 10 mg/kg i.p. Following induction of anesthesia, a laparotomy was performed exposing the liver. Dissections of the median lobe were preformed first removing approximately 25% of the lobe mass followed by treatment and a second injury representing a mid-lobe transaction removing approximately 50% of the lobe mass. Application of the formulation provided in Example 2 applied by irrigation and positive pressure spray techniques were able to control the hemorrhage in all animals (n=8) within 20 seconds (range 10-45 sec) compared with control animals that exsanguinated from the model injuries within 5-10 minutes. The control of hemorrhage was confirmed for a period of 30 minutes and the animals were subsequently euthanized.

Example 30

Hemostasis of Saphenous Vein Transection in a Murine Model

Eight male Sprague-Dawley rats (400-450 g) were anesthetized using ketamine 90 mg/kg and xylazine 10 mg/kg i.p. Following induction of anesthesia, the groin was dissected to expose the superficial saphenous vein. The vein was transected by a single perpendicular incision. Application of the formulation provided in Example 2 applied by irrigation and positive pressure spray techniques were able to control the hemorrhage in all animals (n=8) within 10-45 seconds compared with control animals that exsanguinated from the model injuries within 6-10 minutes. The control of hemorrhage was confirmed for a period of 30 minutes and the animals were subsequently euthanized.

Example 31

Hemostasis of Liver Lacerations in a Porcine Model

A single farm pig weighing approximately 30 kg was anesthetized and a transverse laparotomy was performed to expose the liver. The was transected approximately 2.5 cm from the lateral edge to produce a diffuse capillary bed injury which if left untreated represents an exsanguinating injury in approximately 10 minutes. The injury was treated with an irrigation consisting of Rylo MG 19 (Danisco Corp.) 94.5%, dodecane 5% and epinephrine 0.5%. Following a single application of approximately 10 ml, the bleeding was well controlled with minor oozing noted in the injury bed. A subsequent injury was inflicted by removing a portion of the liver lobe approximately 5 cm from the outer margin. This injury resulted in a widespread capillary bed injury with the transection of multiple arterioles that would result in death in 5 minutes or less without supportive treatment and control. An irrigation of the Rylo/dodecane/epinephrine formulation once again maintained adequate control of the capillary bleeding. It was not adequate for the arterial injuries. However a Rylo/dodecane/epinephrine impregnated gauze was applied to the injury. The application maintained adequate control of the capillary and arterial bleeding while in place. Once the gauze was removed, hemostasis was maintained within the capillary bed; however the arterial injuries were not well controlled.

Example 32

Hemostasis of Traumatic Buccal Laceration

A white 4 yr old female subject presented with a traumatic laceration adjacent to the lower right bicuspids secondary to a playground fall. The laceration bled liberally following attempts to apply pressure and cold compress for approximately 5 minutes. Approximately 1 ml of a formulation disclosed in Example #2 was applied to the injury. Hemostasis was established within 30 seconds without further need for subsequent treatment.

A white 2 yr old female subject presented with a traumatic laceration adjacent to the lower incisors secondary to an inadvertent collision with another child. The laceration bled liberally following attempts to apply pressure and cold compress for approximately 3-5 minutes. Approximately 1 ml of a formulation disclosed in Example #2 was applied to the injury. Hemostasis was established within 30 seconds without further need for subsequent treatment.

Example 33

Hemostasis of Canine Bite

A 38 yr old white male presented with a single puncture wound and laceration approximately 1.5 cm in length on the anterior of the distil phalanx of the left thumb extending to the nail bed that bled freely despite application of direct pressure. Subsequently approximately 0.5 ml of a formulation disclosed in Example #2 was applied to the wound. The initial application formed a gel over the puncture site; however the bleeding was not completely controlled. A subsequent application of the preformed gel was directed into the puncture site with pressure. The second application established hemostasis within 30-45 seconds with only minor oozing of the wound over a period of 2-4 days post injury.

Example 34

Hemostasis—Epistaxis Treatment

A 37 yr old white male with an uneventful past medical history presented with acute, spontaneous epistaxis. Conventional treatment and pressure showed no benefit after 5-10 minutes. The application of approximately 0.25 ml of a formulation disclosed in Example #5 was achieved using a cotton swab. Following application, the nares were pinched for approximately 10 seconds to disperse the material in the nasal cavity. Immediate hemostasis was achieved following the single application without further bleeding.

Example 35

Therapeutic/Protective Wound Care System—Canine Foot Pad Ulcerations

A 9 yr old Yorkshire terrier with a past medical history of diabetes and seizure disorder presented with extensive foot pad ulcerations on all four feet making ambulation increasingly difficult. The animal's left front and right rear pad wounds were cleaned and dressed every other day with the formulations disclosed in Example #2 and 26B respectively; the right front and left rear pads were merely cleaned and dressed without treatment. Over a period of 30 days, the ulcerations of the treated pads improved and healed at a significantly more rapid rate than the untreated pads, which improved little if at all. The treated pads demonstrated resolution of the ulcerations within the 30 day period. Furthermore, one untreated ulcer became infected prior to the conclusion of the 30 day window. The other untreated ulcer became infected in the week following the 30 day period. Both treated ulcers healed with no sign of infection.

Example 36

Protective Wound Care System—Strep Throat

A 36 yr old white male presented with profound pain in the oropharangeal area secondary to acute tonsillitis and strep A infection. A formulation consisting of GMO 85% and PEG 400, 10% and PEG 200, 5% was applied using a cotton swab. The system formed a protective gel coating over the inflamed region allowing relief of pain and the consumption of liquids for approximately a 4 hr period.

The described embodiments of the invention are intended to be merely exemplary and numerous variations and modifications will be apparent to those skilled in the art. Different brands for particular ingredients may be used, and other compounds having similar physicochemical properties may be interchanged with those described to yield alternative formulations with desired hemostatic, wound healing, fluid-absorbing, antimicrobial and/or pain-relieving characteristics. All such variations and modifications are intended to be within the scope of the present invention as defined in the appended claims.

Example 37

Therapeutic/Protective Wound Care System—Burn

A patient suffering from $2^{nd}$ and $3^{rd}$ degree burns is treated with an absorbent article as described in Example 27, wherein a wound dressing article, its surface infused or coated with a wound-healing, fluid-absorbing formulations described in Examples 1-6, 9, 11, 16, 19, 20, and 23 and 24, especially, is applied to the burn area after cleaning. The burn surface is cleaned and dressed every other day, every day, or more frequently, as needed, with a sterile absorbent article containing a formulation as described. As a control, comparable burn areas are treated with other conventional wound dressing articles and burn treatment formulations at the same time, with burn surface cleaning and dressing procedures identical for both control areas and burn areas treated with formulations described herein. The burn areas treated with the absorbent articles infused or coated with formulations as disclosed herein improve and heal at a significantly more rapid rate than the areas being treated with conventional wound dressing articles and burn treatment formulations. Moreover, there is significantly less tissue removal upon dressing change when using absorbent articles and wound dressing articles as disclosed herein, having formulations described above present in or on the wound dressing article material or surface, and faster healing is seen, with less oozing and infection.

Alternatively, the burn area may be treated with formulations from Examples 1-6, 9, 11, 19, 20, 23 or 24 by spraying, coating, bathing, or otherwise applying the formulation directly on the burn area, with the wound dressing material, such as a conventional gauze or other bandage applied after application of the formulation disclosed herein.

Example 38

Protective Wound Care System—Open Sore

A patient suffering from an open sore, such as a bed sore, abrasive burn, caustic burn, or similar wound creating an open, oozing sore, is treated with an absorbent article as described in Example 27, wherein a wound dressing article, its surface infused or coated with a wound-healing, fluid-absorbing formulations described in above Examples is applied to the open sore area after cleaning. The sore surface is cleaned and dressed every other day, every day, or more frequently, as needed, with a sterile absorbent article containing a formulation as described. As a control, comparable sore areas are treated with other conventional wound dressing articles and open sore treatment formulations at the same time, with sore cleaning and dressing procedures identical for both control areas and sore areas treated with formulations described herein. The open sore areas treated with the absorbent articles infused or coated with formulations as disclosed herein improve and heal at a significantly more rapid rate than the areas being treated with conventional wound dressing articles and open sore treatment formulations. Moreover, there is significantly less tissue removal upon dressing change when using absorbent articles and wound dressing articles as disclosed herein, having formulations described above present in or on the wound dressing article material or surface, and faster healing is seen, with less oozing and infection.

Alternatively, the open sore area may be treated with formulations from above-described Examples by spraying, coating, bathing, or otherwise applying the formulation directly on the open sore area, with the wound dressing material, such as a conventional gauze or other bandage, applied after application of the formulation disclosed herein.

The described embodiments of the invention are intended to be merely exemplary and numerous variations and modifications will be apparent to those skilled in the art. Different brands for particular ingredients may be used, and other compounds having similar physicochemical properties may be interchanged with those described to yield alternative formulations with desired hemostatic, wound healing, fluid-absorbing, antimicrobial and/or pain-relieving characteristics. All such variations and modifications are intended to be within the scope of the present invention as defined in the appended claims.

Examples of Anti-Infective, Vascular Closure & Bone Sealant Utility

The following formulations were manufactured and submitted for anti-infective validation testing:

Example 39A

| | |
|---|---|
| Glyceryl monooleate | 93.00% |
| Normal Saline for Injection, USP | 7.00% |

In a 14 day bacteriocidal challenge per Antimicrobial Effectiveness Test, the above composition was inoculated with S. Aureus at $1.3 \times 10^5$ CFU/g, E. Coli at $1.5 \times 10^5$ CFU/g and P. Aeruginosa at $2.7 \times 10^5$ CFU/g. All bacteria were dead at the end of the 14 day period. This example was more effective than a control of pressure alone for the closure of vascular access sites in swine and rabbit models. This formulation is also effective, as are other high viscosity forming formulations disclosed herein, to seal bone tissue both by stream irrigation and manual smear application with excess aqueous liquid.

Example 39B

| | |
|---|---|
| Glyceryl monooleate | 93.00% |
| Ethanol, USP | 1.66% |
| Normal Saline for Injection, USP | 5.34% |

In a 14 day bacteriocidal challenge per Antimicrobial Effectiveness Test, the above composition was inoculated with S. Aureus at $1.3 \times 10^5$ CFU/g, E. Coli at $1.5 \times 10^5$ CFU/g and P. Aeruginosa at $2.7 \times 10^5$ CFU/g. All bacteria were dead at the end of the 14 day period. Example 39B, was also tested and proved utility for the prevention of scar tissue adhesions in the nasal cavity of an adult white male, 38 years of age, as well as in various tissues of rat, swine and human models. When combined with medical absorbent articles such as sterile gauze, it demonstrated the ability to inhibit scar adhesions, speed healing and prevent infections in a canine model. This formulation also inhibits thrombin generation kinetics as do many of the high viscosity formulations within this disclosure. This example was more effective than an control of pressure alone for the closure of vascular access sites in swine and rabbit models.

Example 39C

| | |
|---|---|
| Glyceryl monooleate | 92.53% |
| Lauric Acid | 0.25% |
| Capric Acid | 0.22% |
| Ethanol, USP | 1.66% |
| Normal Saline for Injection, USP | 5.34% |

In a 14 day bacteriocidal challenge per Antimicrobial Effectiveness Test, the above composition was inoculated with S. Aureus at $1.3 \times 10^5$ CFU/g, E. Coli at $1.5 \times 10^5$ CFU/g and P. Aeruginosa at $2.7 \times 10^5$ CFU/g. All bacteria were dead at the end of the 14 day period.

Example 39D

| | |
|---|---|
| Glyceryl monooleate | 91.37% |
| Lauric Acid | 0.88% |
| Capric Acid | 0.75% |
| Normal Saline for Injection, USP | 7.00% |

In a 14 day bacteriocidal challenge per Antimicrobial Effectiveness Test, the above composition was inoculated with S. Aureus at $1.3 \times 10^5$ CFU/g, E. Coli at $1.5 \times 10^5$ CFU/g and P. Aeruginosa at $2.7 \times 10^5$ CFU/g. All bacteria were dead at the end of the 14 day period.

Example 39E

| | |
|---|---|
| Glyceryl monooleate | 90.21% |
| Lauric Acid | 1.50% |
| Capric Acid | 1.29% |
| Ethanol, USP | 3.330% |
| Normal Saline for Injection, USP | 3.68% |

In a 14 day bacteriocidal challenge per Antimicrobial Effectiveness Test, the above composition was inoculated with S. Aureus at $1.3 \times 10^5$ CFU/g, E. Coli at $1.5 \times 10^5$ CFU/g and P. Aeruginosa at $2.7 \times 10^5$ CFU/g. All bacteria were dead at the end of the 14 day period.

Examples of Biocompatibility Void Fillers and Tissue Growth/Healing Promotion

The following formulations were manufactured and submitted for implant testing:

Example 40A

| | |
|---|---|
| Glyceryl monooleate | 93.00% |
| Normal Saline for Injection, USP | 7.00% |

The above formulation was submitted for standardized protocol driven toxicity, hypersensitivity and irritation testing including ISO Elution Test (MEM Extract), ISO Agar Diffusion Testing, ISO Maximization Test for Delayed Hypersensitivity and ISO Intracutaneous (Intradermal) Reactivity Test. In all replications the formulation was found to be non-cytotoxic by multiple methods, to have no sensitization potential by multiple methods and to have no irritation potential by multiple methods.

The above formulation was injected SQ into Sprague Dawley® rats and filled into brain tissue voids created by sham surgeries. Blinded pathologists reviewed the histology of fixed tissue slides for both SQ and brain depositions. Summary of SQ Findings: (1 cc dose at 45 days)—Tissue is well organized with collagen and vessels apparently up regulated in the margins of the deposit; some macrophages present, but no granulomatous inflammation, no giant cells or foreign body granulomas present. (0.5 cc dose at 45 days)—Smaller doses of 0.5 cc show similar vessel up regulation with considerably less collagen up regulation suggesting that the size of the dose itself significantly contributes to the initial collagen response; no giant cell or otherwise granulomatous inflammation. (1 cc dose at 90 days)—Deposit is dramatically reduced in size and organization; small islands of deposit with up-regulated vessels and normal tissue in between have replaced the 45 day bolus deposit; the deposit is apparently being resorbed by a non-capsular means and normal tissue now resides in the former occupied space. Summary of Brain Void Filler Findings: All animals gained weight (19%-26%); showed no signs of systemic toxicity; showed no focal or gross neurological deficits. No collagen up regulation in field; all formerly traumatized tissue grossly normal at 30 days onward.

Figure 13:
FIG. 13 is a low magnification image of up-regulated peripheral vasculature in a rat after a 1 cc implant of the formulation in Example 40A, implanted subcutaneously into a rat which was sacrificed at 45 days.
Figure 14:
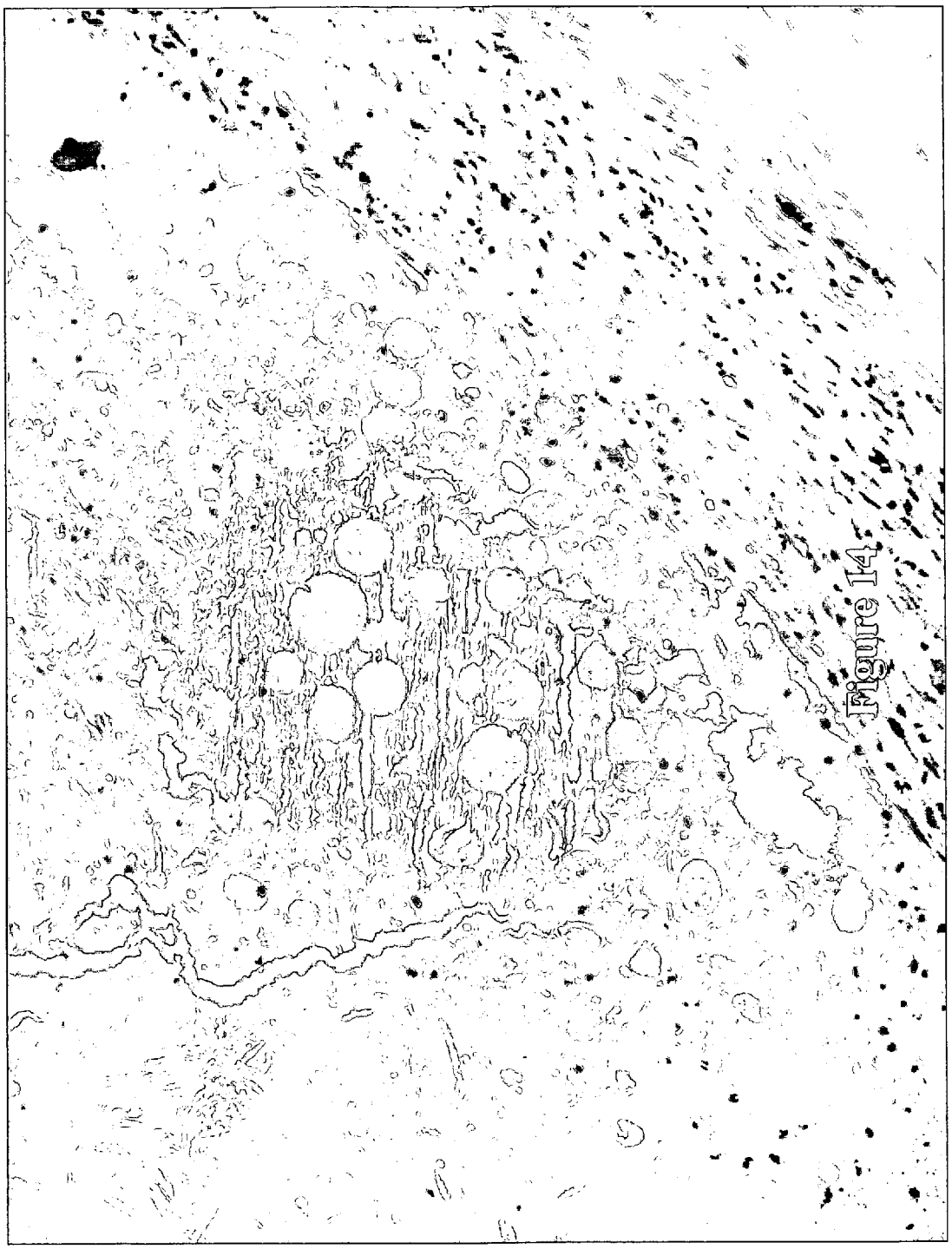
FIG. 14 is a high magnification image of up-regulated collagen and surrounding vasculature in a rat after a 1 cc implant of the formulation in Example 40A, implanted subcutaneously into a rat which was sacrificed at 45 days.
Figure 15:
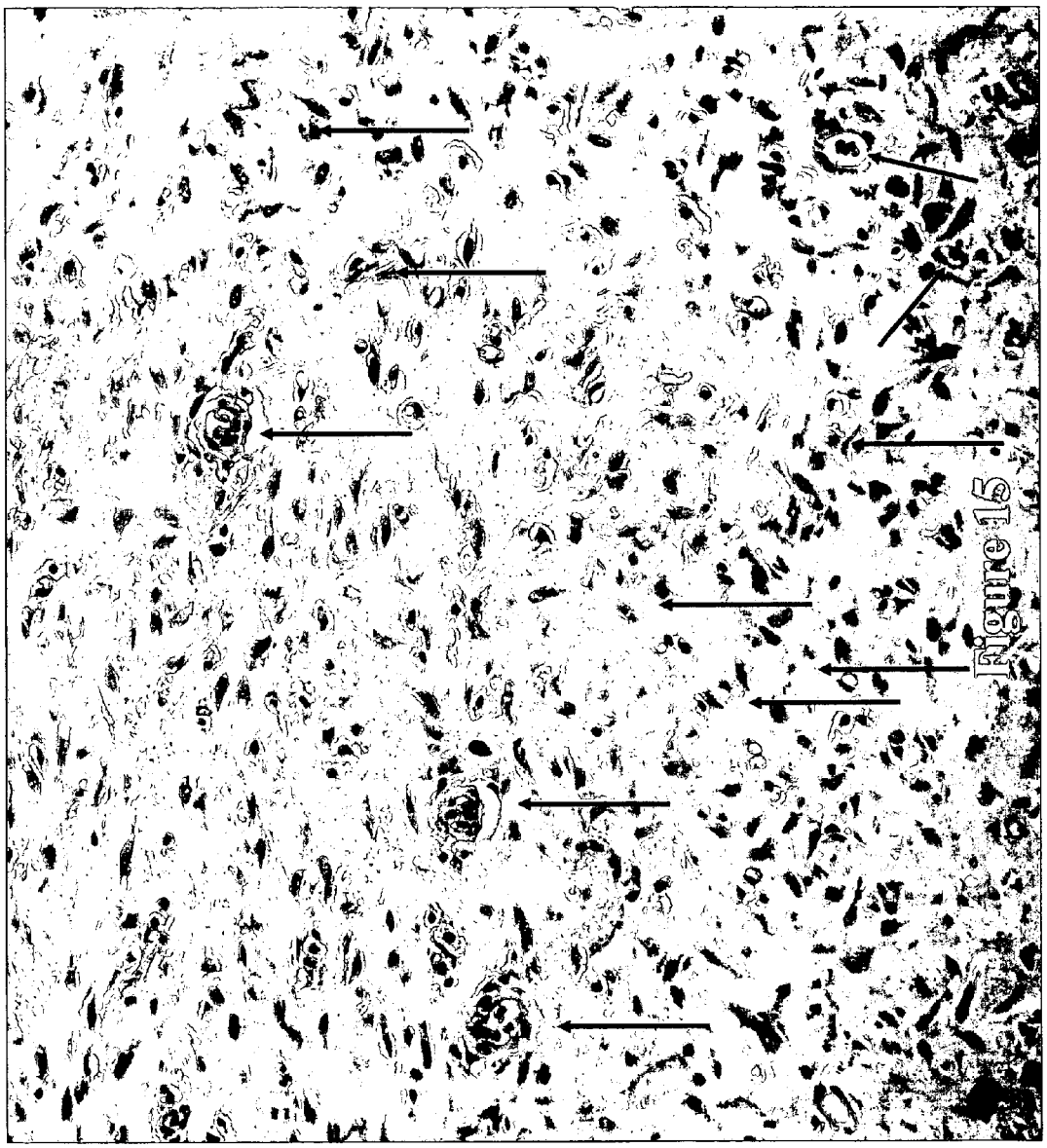
FIG. 15 is a high magnification image of up-regulated peripheral vasculature in a rat after a 1 cc implant of the formulation in Example 40A, implanted subcutaneously into a rat which was sacrificed at 45 days.

As can be seen in FIG. 13, a low magnification image, up-regulated peripheral vasculature is apparent in rat tissue after 1 cc of the formulation in Example 40A (above) was implanted subcutaneously into a rat, which was then sacrificed at 45 days. Similarly, FIGS. 14 and 15 are high magnification images showing up-regulated collagen and surrounding vasculature (FIG. 14) or up-regulated vasculature (FIG. 15) in rat tissue after 1 cc of the formulation in Example 40A was implanted subcutaneously into a rat, which was sacrificed again at 45 days.

Figure 16:
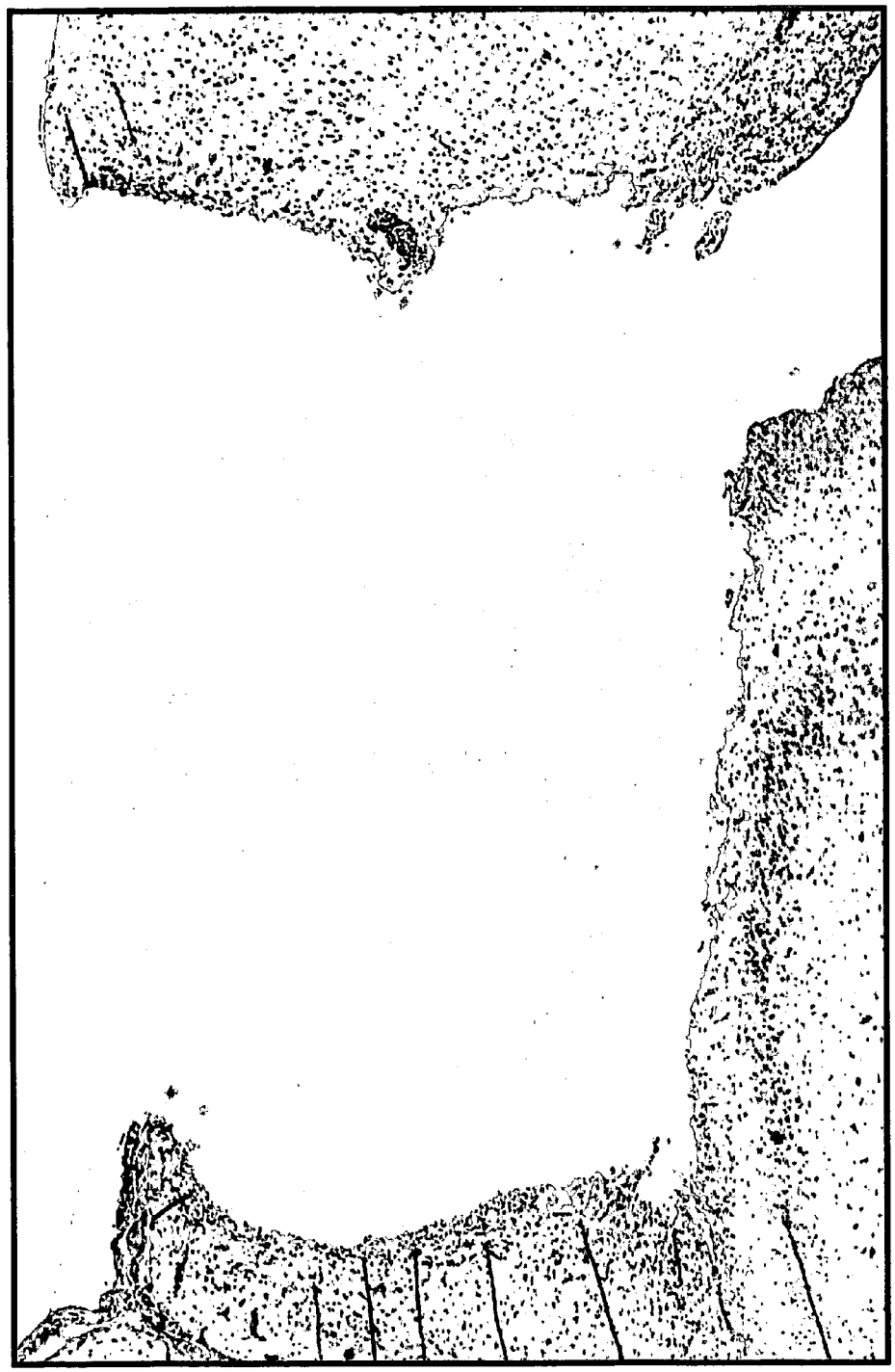
FIG. 16 is an image of a rat brain section showing a tissue void created by a surgical procedure (sham surgery). The formulation of Example 40A was used to fill the void created by the surgical procedure, and approximately 5 mg of the formulation was inserted into the 3×3×3 mm void. The picture shows that the surrounding tissue is effectively normal after 30 days.

In addition, FIG. 16 is an image of a rat brain section showing a tissue void created by a surgical procedure (sham surgery). The formulation of Example 40A was used to fill the void created by the surgical procedure, and approximately 5 mg of the formulation was inserted into the 3×3×3 mm void. The picture shows that the surrounding tissue is effectively normal after 30 days.

Similar or Better Histology Results were Found with Subcutaneous Injections of the Following Formulations Example 40B

| Glyceryl monooleate | 93% |
|---|---|
| Ethanol, USP | 1% |
| Normal Saline for Injection, USP | 6% |

Example 40C

| Glyceryl monooleate | ~93% |
|---|---|
| VEGF | ~10 ng/ml |
| Albumin | ~0.001% |
| Ethanol, USP | ~1% |
| Normal Saline for Injection, USP | ~6% |

Example 40D

| Glyceryl monooleate | 91% |
|---|---|
| 1-Stearoyl-2-arachidonoyl-sn-glycerol | 2% |
| Ethanol, USP | 1% |
| Normal Saline for Injection, USP | 6% |

Example 40E

| Glyceryl monooleate | 90% |
|---|---|
| PEG 600 | 10% |

Examples of Dental Tissue Void Fillers

The following formulations were manufactured and tested as dental tissue void filler:

Example 41

| Ethanol, USP | 0.7% |
|---|---|
| Normal Saline for Injection, USP | 4.2% |
| Benzocaine | 7% |
| Calcium Carbonate | 30% |
| Glycerol monooleate | 58.1% |

Example 41B

| Ethanol, USP | 0.7% |
|---|---|
| Normal Saline for Injection, USP | 4.2% |
| Eugenol | 7% |
| Calcium Carbonate | 30% |
| Glycerol monooleate | 58.1% |

In both examples, ethanol and normal saline was mixed thoroughly and heated to approximately 40° C. in separate closed containers. Glyceryl Monooleate (GMO) was heated to melting in separate containers. Benzocaine was added to the water/ethanol mixture of 41A while Eugenol was added to the melted GMO of 41B. The respective contents of the solvents and GMO containers were then combined under vigorous mixing for 10 minutes, and then the Calcium Carbonate was added under continuous agitation for another 10 minutes while allowing to continue to cool to room temperature. The resulting mixtures produced an off white paste.

The present examples possessed characteristics making them operable as hemostatic, fluid-controlling, dental void filler formulations for delivery by means of manual insertion into a dry socket resulting from tooth extractions. Both formulations were effective in temporarily filling and obturating the extraction void. While further testing is required to optimize and thoroughly evaluate these compositions, the single human patient in the test stated a preference for formulation 41B.

Examples of Utility in Cosmetic Medical Applications

Example 42A

| Glyceryl Monooleate | 70% |
|---|---|
| Glyceryl Monostearate | 15% |
| Cottonseed Oil, NF | 15% |

The Glyceryl Monooleate (GMO) was heated to melting and the Cottonseed Oil was added with thorough mixing. The Glyceryl Monostearate (GMS) was added. The combined mixture was heated until molten and mixed well and allowed to cool. The resulting mixture produced a white to off-white composition with a semisolid consistency.

Example 42B

| Glyceryl Monooleate | 80% |
|---|---|
| Glyceryl Monostearate | 10% |
| Cottonseed Oil, NF | 10% |

The Glyceryl Monooleate (GMO) was heated to melting and the Cottonseed Oil was added with thorough mixing. The Glyceryl Monostearate (GMS) was added. The combined mixture was heated until molten and mixed well and allowed to cool. The resulting mixture produced a white to off-white composition with a semisolid consistency.

The present examples possessed characteristics making them operable as biodegradable breast implant media. The present systems exhibited gel texture characteristics similar to silicone gel implant media when tested on a TA.XT Plus Texture Analyzer (Stable Microsystems) and are non-toxic substitutes that mimic soft tissues. Further testing in filled breast implant also gave results similar to silicone implants.

Example 43A

| Glyceryl Monooleate | 70% |
|---|---|
| Glyceryl Monostearate | 15% |
| Glycerin | 15% |

The Glyceryl Monooleate (GMO) was heated to melting and the Glycerin was added with thorough mixing. The Glyceryl Monostearate (GMS) was added. The combined mixture was heated until molten and mixed well and allowed to cool. The resulting mixture produced a white to off-white composition with a semisolid consistency.

Example 43B

| Glyceryl Monooleate | 80% |
|---|---|
| Glyceryl Monostearate | 10% |
| Glycerin | 10% |

The Glyceryl Monooleate (GMO) was heated to melting and the Glycerin was added with thorough mixing. The Glyceryl Monostearate (GMS) was added. The combined mixture was heated until molten and mixed well and allowed to cool. The resulting mixture produced a white to off-white composition with a semisolid consistency.

Example 43C

| Glyceryl Monooleate | 88% |
|---|---|
| Water for Injection, USP | 12% |

The Glyceryl Monooleate (GMO) and the Water for injection was heated to approximately 45° C. and combined with thorough mixing. The resulting mixture produced a hazy gel composition with a semisolid consistency.

Examples of Crosslinking Agents

The following formulations were manufactured and submitted for residence time testing:

Example 44A

| Glyceryl monooleate | 93.00% |
|---|---|
| Water for Injection, USP | 7.00% |
| or | |
| 2% Glutaraldehyde Aqueous Solution | 7.00% |

A method for evaluating residence time was developed. Tissue samples were soaked in pH 2.5 aqueous solution at 37° C. for not less than 4 hours. The tissues were then treated with controlled doses of liquid-crystal forming compound formulations and allowed to soak in pH 2.5 aqueous solution at 37° C. for 60 minutes. The above formulations were subjected to the residence time test method described above. The formulation above, while using Water for Injection as the solvent, migrated from the tissue site in less than 10 minutes. The same formulation, when tested comprising 2% glutaraldehyde solution instead of Water for Injection, remained in place for over 60 minutes. Therefore, the present examples comprising the crosslinking agent possessed characteristics making it operable to significantly increase residence time. Formulation 44A, without the 2% Glutaraldehyde aqueous solution, will provide increased residence time with the simple addition of 1% gelatin as a viscosity enhancer.

Example 44B

| Glyceryl monooleate | 93.00% |
|---|---|
| Whole Blood | 7.00% |
| 2% formaldehyde & 1% Vanillin Aq. Soln. mixed in situ | 2 drops |

Example 44C

| Glyceryl monooleate | 93.00% |
|---|---|
| Glutaraldehyde 2% & 1% Vanillin Aqueous Solution | 7.00% |

The above formulations were subjected to the residence time test method described above. The formulations above both remained in place for over 60 minutes. Therefore, the present examples, comprising the crosslinking agent, and in the case of Example 44B also a crosslinkable substrate, possessed characteristics making them operable to significantly increase residence time.

What is claimed is:

1. A therapeutic formulation adapted for positive-pressure application and effective for controlling biological fluid at a desired site in a subject, the formulation comprising:

(i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof;

(ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof;

wherein the formulation effectively controls biological fluid at the desired site in the subject by being in a liquid crystalline state or capable of forming a liquid crystalline state after application to the desired site.

2. A therapeutic formulation according to claim 1, wherein the solvent is selected from the group consisting of a polar solvent, a non-polar solvent, a semi-polar solvent, and a combination thereof.

3. An absorbent article comprising (a) an absorbent layer comprising a liquid-permeable and moisture vapor-permeable outer layer having an inner surface and an outer surface, the inner surface essentially coextensive with an outer surface of the absorbent layer; (b) a liquid-permeable liner, adapted to be non-adherent to a wound, having a surface that is substantially coextensive with an inner surface of the absorbent layer such that the absorbent layer is located between the liquid-permeable liner and the outer layer; and (c) a formulation effective for controlling biological fluid of a subject is present on at least a portion of a surface of the liquid-permeable liner opposite that which is coextensive with the inner surface of the outer layer, wherein the formulation comprises:

(i) from about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof;

(ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof;

wherein the formulation effective for controlling biological fluids provides utility as an anti-adherent between the article and bodily tissue to assist in placement or removal of the article from a site of use thereby reducing trauma from application or removal of said article.

4. An infection resistant device for location at a desired site of a subject, the device comprising:

an anti-infective formulation of (i) about 25% to 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof;

(ii) solvent; and (iii) therapeutic agent, which is a fatty acid combination selected from the group consisting of caprylic acid, capric acid, lauric acid, myristic acid, myristoleic acid, palmitic acid, palmitoleic acid, oleic acid, and pharmaceutically acceptable salts thereof;

wherein said anti-infective formulation inhibits the formation of pathogen growth including microbial biofilms on the device, or in adjacent tissues, thereby imparting infection resistance.

5. An infection resistant device according to claim 4, wherein the liquid-crystal forming compound is glyceryl monooleate.

6. An infection resistant device according to claim 5, wherein upon formation of a viscous liquid crystalline state, the anti-infective formulation thereby increases residence time and decreases a tendency to migrate from the device location at the desired site of the subject.

7. An infection resistant device according to claim 6, wherein the liquid crystal formulation releases degradation products of the liquid-crystal forming compound from the formulation, wherein said degradation products provide an additional anti-infective effect.

8. An infection resistant device according to claim 7, wherein the device is effective for treatment of a wound.

9. An infection resistant device according to claim 5, wherein the device is selected from the group consisting of a medical sponge, a surgical dressing, a wound dressing, an adhesive bandage, and a combination thereof.

10. An infection resistant device according to claim 4, wherein the device is selected from the group consisting of a prosthetic, an implant, and a combination thereof.

11. A thrombin inhibitor formulation comprised of (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; (iii) and a fatty acid combination selected from the group consisting of caprylic acid, capric acid, lauric acid, myristic acid, myristoleic acid, palmitic acid, palmitoleic acid, oleic acid, and pharmaceutically acceptable salts thereof; wherein the formulation is adapted for positive pressure application to desired site in a subject.

12. A thrombin inhibitor formulation according to claim 11, wherein the liquid-crystal forming compound is glyceryl monooleate.

13. A thrombin inhibitor formulation according to claim 11, wherein the formulation is a neuroprotective agent.

14. A medical cosmetic formulation effective for mimicking soft tissue at a desired site in a subject, the formulation comprising: (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof; and optionally, other compounds to provide viscosities and textures effective for mimicking soft tissue.

15. A method for effectively controlling biological fluid at a desired site in a subject, the method comprising: administering by positive pressure an effective amount of a therapeutic formulation according to claim 1 at the site for a period of time effective to control biological fluid at the desired site.

16. A method for effectively controlling biological fluid at a desired site in a subject, the method comprising: administering an effective amount of a formulation according to claim 1 for a period of time effective to control biological fluid at the desired site.

17. A method according to claim 15, wherein the formulation is a liquid, a gel or a semi-solid.

18. A method according to claim 15, wherein the formulation forms a cubic phase after application to the site.

19. A method according to claim 15, wherein the formulation forms a viscous phase prior to application to the site.

20. A method according to claim 15, wherein effectively controlling biological fluid further comprises: promoting hemostasis at the desired site.

21. A method according to claim 15, wherein effectively controlling biological fluid further comprises: promoting coagulation at the desired site.

22. A method according to claim 15, wherein effectively controlling biological fluid further comprises: facilitating healing by inducing local effects at the desired site.

23. A method according to claim 22, wherein facilitating healing further comprises: maintaining moisture at the desired site, wherein the desired site is a burn.

24. A method according to claim 15, wherein effectively controlling biological fluid further comprises: providing a formulation in the form of a tissue filler having increased residence time at or near the desired site, such that the formulation resists bodily clearance.

25. A method according to claim 24, wherein the tissue filler is a dermal filler, a bone filler, a brain filler, a synovial filler or a muscle filler.

26. A method according to claim 15, wherein effectively controlling biological fluid further comprises: forming a protective sealant at the desired site, so as to control flow and exchange of biological fluids and promote sealing of tissue via formation of the protective sealant barrier at the site.

27. A method according to claim 15, wherein effectively controlling biological fluid further comprises: retarding the formation of a surgical adhesion, so as to inhibit the formation of undesired post-operative scar tissue that may result at or adjacent to a site of surgical intervention.

28. A method according to claim 15, wherein the desired site is part of the female gynecological region, including the vagina, uterus, or cervix.

29. A method according to claim 15, wherein the site is an acute trauma wound or a chronic wound.

30. A method according to claim 15, wherein administering further comprises: administering to the site by laparoscopy, endoscopy, irrigation, continuous spray, intermittent spray, continuous stream, intermittent stream, lavage, douche, enema, suppository, implant, deposition, direct or indirect manual administration or by incorporation into a medical article.

31. A method for effectively controlling blood loss at a desired site of a subject, the method comprising: administering by positive pressure an effective amount of a thrombin inhibitor formulation at the desired site for a period of time effective to control blood loss at the desired site, wherein the formulation comprises (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iiii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof.

32. A method for effectively sealing a tissue or filling a tissue void at a desired site of a subject, the method comprising: administering by positive pressure an effective amount of a thrombin inhibitor formulation at the desired site for a period of time effective to seal the tissue or fill the tissue void, wherein the formulation comprises about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof.

33. A method for controlling blood loss at a site in a subject, the method comprising: administering the thrombin inhibitor formulation of claim 11 at a site of blood loss in a subject, wherein the formulation facilitates blood coagulation, thereby controlling blood loss at the site.

34. A method according to claim 32, wherein administering further comprises: filling a tissue void created by trauma, disease or a surgical procedure.

35. A method for administering the therapeutic formulation according to claim 1, the method comprising: administering an effective amount of the formulation directly to a vascular access site of a venous or arterial tissue of a subject.

36. A method for administering the therapeutic formulation according to claim 35, wherein the formulation is administered so as to contact tissue adjacent to the vascular access site in the subject.

37. A method according to claim 35, wherein administering further comprises delivering the formulation topically to superficial tissue of the venous or arterial tissue of the access site.

38. A method according to claim 35, wherein administering further comprises utilizing an implant article for administering which has been impregnated with the formulation.

39. A method for administering by positive pressure a therapeutic formulation to a desired tissue site in a subject, the method comprising: administering an effective amount of the formulation to the desired tissue site to effect tissue sealing, wherein the formulation comprises (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof; wherein the tissue is selected from the group consisting of epithelial, connective, skeletal, glandular, muscular, and neural tissue.

40. A method according to claim 39, wherein administering further comprises administering to the desired tissue site is a neural tissue site, to control flow of neural biological fluid, including any solute or dispersed substance it may contain, to inhibit of paralysis.

41. A method according to claim 39, wherein the desired site is a bone tissue site with a bone opening, the formulation administered to plug and seal a the bone opening, thereby inhibiting loss of bone tissue biological fluid and providing a protective barrier at the opening.

42. A method according to claim 39, wherein effecting tissue sealing further comprises: filling a tissue void created by trauma or a surgical procedure.

43. A method according to claim 39, wherein administering further comprises: administering to the site by laparoscopy, endoscopy, irrigation, continuous spray, intermittent spray, continuous stream, intermittent stream, lavage, douche, enema, implant, deposition, direct manual applications or by incorporation into a medical article.

44. A method for facilitating effective closure of a vascular wound or incision site at a desired site in a subject, the method comprising: administering an effective amount of a biocompatible biodegradable therapeutic formulation at the vascular wound site or incision site, the formulation comprising: (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, glycyl monoarachidonate, propylene glycyl monolinoleate, propylene glycyl monolinolenate, propylene glycyl monopalmitoleate, propylene glycyl monooleate, and combinations thereof; (ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof; wherein the formulation effects hemostasis by physically staunching blood flow, absorbing fluid, and induces local effects at the site within about 10 minutes or less of administration at the site, thereby facilitating effective closure of the vascular wound or incision.

45. A method for delivering a formulation as claimed in claim 1 to a desired site in a subject, the method comprising: delivering the formulation to the desired site by injection.

46. A method for administering the formulation according to claim 45 wherein the desired site is the circulatory system and the formulation is injected directly within the circulatory system of the subject.

47. A method according to claim 46, wherein injecting further comprises effecting embolization therapy.

48. A method for inhibiting tissue adhesion to a medical article, the method comprising: coating said medical article with a formulation as claimed in claim 1, thereby inhibiting tissue adhesion to said article and reducing pain and trauma upon application and subsequent removal of the medical article.

49. A method for sterilizing a formulation or device containing said formulation, the formulation as claimed in claim 1, the method comprising: sterile filtering, distilling, thermally exposing, exposing to ionizing radiation, aseptically processing, heating steam under pressure, or exposing to a gas the formulation or device containing the formulation prior to use.

50. A method for effectively mimicking soft bodily tissues at a desired site in a subject, the method comprising: administering an effective amount of a formulation as claimed in claim 14 internally at the desired site to mimic the soft tissue.

51. A therapeutic formulation according to claim 1, wherein the fatty acid ester is at least glyceryl monooleate.

52. A formulation according to claim 1, wherein the fatty acid combination is at least capric acid and lauric acid.

53. A formulation according to claim 1, wherein the solvent is a polar solvent selected from the group consisting of water, an aqueous liquid, a biological fluid, an alkanol, a polyethylene glycol, a propylene glycol, a polypropylene glycol, a glycol, a glycerin, an isotonic aqueous solution, a physiologic buffered system, and a combination thereof.

54. An anti-infective formulation adapted for positive-pressure application and effective for inhibiting the growth or killing one or more microbial pathogens, or a biofilm at a desired site, the formulation comprising: (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; (iii) about 1% to about 30% by weight fatty acid combination selected from the group consisting of caprylic acid, capric acid, lauric acid, myristic acid, myristoleic acid, palmitic acid, palmitoleic acid, oleic acid, and pharmaceutically acceptable salts thereof; and (iv) a therapeutic agent, wherein the formulation effectively inhibits the growth or kills the one or more microbial pathogens at the desired site relative to growth or presence of microbial pathogens in the absence of the formulation.

55. An anti-infective formulation according to claim 54, wherein the formulation provides increased residence time and decreased tendency to migrate from the desired site by forming a viscous liquid crystalline state.

56. An anti-infective formulation according to claim 54, wherein the liquid crystal formulation releases degradation products of the liquid-crystal forming compound from the formulation, wherein said degradation products provide an anti-infective effect.

57. An anti-infective formulation according to claim 56, wherein the formulation is effective for treatment of a wound created by trauma, surgical procedures, leg ulcers, decubitus ulcers, fungal ulcers, diabetic ulcers, foot ulcers, sacral ulcers, or indolent ulcers.

58. A method for inhibiting the growth or killing pathogens at a desired site of a subject, the method comprising: administering by positive pressure an effective amount of anti-infective formulation at the site comprising (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof; wherein the formulation is in a liquid crystalline state or forms a liquid crystalline state after application to the desired site.

59. A method according to claim 58, wherein the formation of a viscous liquid crystalline state increases the residence time and decreases the tendency of more fluid states to migrate from the desired site, including bodily tissues and implant devices.

60. A method according to claim 58, wherein the liquid-crystal forming compound serves as precursor to at least one degradation product which provides an anti-infective effect.

61. A method according to claim 58, wherein the anti-infective formulation comprises up to about 50% fatty acid combination.

62. A method according to claim 58, wherein administering to the desired site further comprises treating an acute or chronic wound including an abrasion, a burn, a laceration, a puncture, an incision, a surgical wound, an ulceration, a leg ulcer, a decubitus ulcer, a fungal ulcer, a diabetic ulcer, a foot ulcer, a sacral ulcer, an indolent ulcer or a combination thereof.

63. A method according to claim 58, wherein administering comprises physically coating or applying said formulation to any implantable device for the prevention of pathogen growth or to kill pathogens that attempt to colonize upon the implant device including a biofilm or infect a subject in the post operative period from the implant site.

64. A method for effectively controlling biological fluid at an inflamed tissue desired site of a subject, the method comprising: administering by positive pressure an effective amount of a formulation comprising (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof; at the site for a period of time effective to control biological fluid at the desired site thereby reducing inflammation.

65. A method of increasing residence time of a liquid crystal formulation at a desired site in a subject and decreasing the tendency for migration of the formulation from that site, the formulation comprising (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof; the method comprising:
  (a) forming the liquid-crystal formulation in a viscous liquid crystalline state by incorporating an effective amount of the liquid-crystal forming compound; and
  (b) contacting the liquid-crystal formulation with the desired site, thereby increasing the residence time and decreasing the tendency for migration from the desired site.

66. A method of increasing residence time of a liquid crystal formulation at a desired site in a subject and decreasing the tendency for migration of the formulation from that site, the formulation comprising (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof; the method comprising:
  (a) incorporating an effective amount of a viscosity enhancer or a mixture thereof into the formulation to decrease the formulation fluidity; and
  (b) contacting the liquid-crystal formulation with the desired site, thereby increasing the residence time and decreasing the tendency for migration from the desired site.

67. The method according to claim 66, wherein the viscosity increasing compound or mixture thereof is selected from the group consisting of a polymer, a fatty acid, a carbohydrate, a glycoprotein, a protein, a peptide, and a combination thereof.

68. The method according to claim 67, wherein the viscosity increasing compound or mixture thereof is selected from the group consisting of gelatin, collagen, lauric acid, capric acid, and a combination thereof.

69. A method of increasing residence time of a liquid crystal formulation at a desired site in a subject and decreasing the tendency for migration of the formulation from that site, the formulation comprising (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof; the method comprising:
  (a) designing the formulation to include a substrate, selected from the group consisting of a substrate with one reactive group, a substrate with a plurality of active groups, and a combination thereof, wherein said groups can be crosslinked by a crosslinking agent selected from the group consisting of a crosslinking compound, a crosslinking promoter, and a combination thereof, by any initiation method to decrease the formulation fluidity; and
  (b) contacting the liquid-crystal formulation with the desired site, thereby increasing the residence time and decreasing the tendency for migration from the desired site.

70. The method according to claim 69, wherein the substrate is a substrate with a plurality of active groups, the substrate containing a nitrogen group, a sulfur group, a vinyl group, an oxygen group or a combination thereof.

71. The method according to claim 70, wherein the substrate is selected from the group consisting of gelatin, gelatin hydrolysates, collagen, collagen hydrolysates, albumin, whey protein, soy protein, casein, casein derivatives, and a combination thereof.

72. The method according to claim 69, wherein the crosslinking agent is selected from the group consisting of an aldehyde derivative including formaldehyde and glutaraldehyde, a vinyl crosslinking agent, a cresol, a phenol, a resorcinol, a eugenol, a vanillin, a vanillin derivative, and a combination thereof.

73. A method of increasing residence time of a liquid crystal formulation at a desired site in a subject and decreasing the tendency for migration of the formulation from that site, the formulation comprising (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof; the method comprising:
(a) designing the formulation to include a crosslinking agent selected from the group consisting of crosslinking compounds, crosslinking promoters, and a combination thereof; and
(b) contacting the liquid-crystal formulation with the desired site, thereby increasing the residence time and decreasing the tendency for migration from the desired site.

74. A method according to claim 73, wherein the crosslinking agent is selected from the group consisting of an aldehyde derivative including formaldehyde and glutaraldehyde, a vinyl crosslinking agent, a cresol, a phenol, a eugenol, a resorcinol, a vanillin, a vanillin derivative, and a combination thereof.

75. A method for effectively inhibiting formation of a surgical adhesion at a desired site of a subject, the method comprising: administering by positive pressure an effective amount of a thrombin inhibitor formulation at the desired site for a period of time effective to form a barrier to the surgical adhesion such that the formation of a surgical adhesion is inhibited, wherein the formulation comprises (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof.

76. A method for effectively treating a wound at a desired site of a subject, the method comprising: administering by positive pressure an effective amount of a thrombin inhibitor formulation at the desired site for a period of time effective to treat the acute or chronic wound, wherein the formulation comprises (i) about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof; (ii) solvent; and (iiii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof.

77. A method according to claim 36, wherein administering further comprises utilizing an implant article for administering which has been impregnated with the formulation.

78. A method according to claim 39, wherein the method further comprises: forming a protective sealing barrier at the desired site, so as to control flow and loss of biological fluid and promote sealing of tissue via formation of the protective sealing barrier at the site.

79. A method according to claim 78, wherein forming the protective sealing barrier further comprises impeding intimate contact and exchange of bodily fluid containing physiological stimulants for scarring between tissues, thereby retarding formation of surgical adhesions at or adjacent to a site of surgical intervention.

80. A method according to claim 79, wherein the formulation further comprises a scar tissue growth inhibitor selected from the group consisting of an antineoplastic agent, an anti-inflammatory agent, an antibiotic agent, an irritant, and a combination thereof.

81. An absorbent article according to claim 3, wherein the formulation inhibits adhesion of the article to tissue.

82. An infection resistant device according to claim 5, wherein the device is a wound dressing and the anti-infective formation inhibits adhesion of the wound dressing to tissue, thereby reducing pain during dressing changes.

83. A formulation according to claim 1, wherein the liquid-crystal forming compound is at least glyceryl monooleate.

84. A formulation according to claim 1, wherein the liquid-crystal forming compound is glyceryl monooleate.

85. A formulation according to claim 84, wherein the fatty acid combination is at least capric acid and lauric acid.

86. An absorbent article according to claim 3, wherein the liquid-crystal forming compound is at least glyceryl monooleate.

87. An absorbent article according to claim 86, wherein the fatty acid combination is at least capric acid and lauric acid.

88. An absorbent article according to claim 3, wherein the liquid-crystal forming compound is glyceryl monooleate.

89. An absorbent article according to claim 3, wherein the fatty acid combination is at least capric acid and lauric acid.

90. An infection resistant device according to claim 4, wherein the liquid-crystal forming compound is at least glyceryl monooleate.

91. An infection resistant device according to claim 90, wherein the fatty acid combination is at least capric acid and lauric acid.

92. An infection resistant device according to claim 4, wherein the fatty acid combination is at least capric acid and lauric acid.

93. An infection resistant device according to claim 92, wherein the liquid-crystal forming compound is glyceryl monooleate.

94. An anti-infective formulation according to claim 54, wherein the liquid-crystal forming compound is at least glyceryl monooleate.

95. An anti-infective formulation according to claim 94, wherein the fatty acid combination is at least capric acid and lauric acid.

96. An anti-infective formulation according to claim 54, wherein the liquid-crystal forming compound is glyceryl monooleate.

97. An anti-infective formulation according to claim 54, wherein the fatty acid combination is at least capric acid and lauric acid.

98. A method according to claim 31, wherein the liquid-crystal forming compound is at least glyceryl monooleate.

99. A method according to claim 98, wherein the fatty acid combination is at least capric acid and lauric acid.

100. A method according to claim 31, wherein the liquid-crystal forming compound is glyceryl monooleate.

101. A method according to claim 31, wherein the fatty acid combination is at least capric acid and lauric acid.

102. A method according to claim 32, wherein the liquid-crystal forming compound is at least glyceryl monooleate.

103. A method according to claim 102, wherein the fatty acid combination is at least capric acid and lauric acid.

104. A method according to claim 32, wherein the liquid-crystal forming compound is glyceryl monooleate.

105. A method according to claim 32, wherein the fatty acid combination is at least capric acid and lauric acid.

106. A method according to claim 39, wherein the liquid-crystal forming compound is at least glyceryl monooleate.

107. A method according to claim 106, wherein the fatty acid combination is at least capric acid and lauric acid.

108. A method according to claim 39, wherein the liquid-crystal forming compound is glyceryl monooleate.

109. A method according to claim 39, wherein the fatty acid combination is at least capric acid and lauric acid.

110. A method according to claim 48, wherein the liquid-crystal forming compound is at least glyceryl monooleate.

111. A method according to claim 110, wherein the fatty acid combination is at least capric acid and lauric acid.

112. A method according to claim 48, wherein the liquid-crystal forming compound is glyceryl monooleate.

113. A method according to claim 48, wherein the fatty acid combination is at least capric acid and lauric acid.

114. A method according to claim 49, wherein the liquid-crystal forming compound is at least glyceryl monooleate.

115. A method according to claim 114, wherein the fatty acid combination is at least capric acid and lauric acid.

116. A method according to claim 49, wherein the liquid-crystal forming compound is glyceryl monooleate.

117. A method according to claim 49, wherein the fatty acid combination is at least capric acid and lauric acid.

118. A method according to claim 58, wherein the liquid-crystal forming compound is at least glyceryl monooleate.

119. A method according to claim 118, wherein the fatty acid combination is at least capric acid and lauric acid.

120. A method according to claim 58, wherein the liquid-crystal forming compound is glyceryl monooleate.

121. A method according to claim 58, wherein the fatty acid combination is at least capric acid and lauric acid.

122. A method according to claim 75, wherein the liquid-crystal forming compound is at least glyceryl monooleate.

123. A method according to claim 122, wherein the fatty acid combination is at least capric acid and lauric acid.

124. A method according to claim 75, wherein the liquid-crystal forming compound is glyceryl monooleate.

125. A method according to claim 75, wherein the fatty acid combination is at least capric acid and lauric acid.

126. A method according to claim 76, wherein the liquid-crystal forming compound is at least glycerol monooleate.

127. A method according to claim 126, wherein the fatty acid combination is at least capric acid and lauric acid.

128. A method according to claim 76, wherein the liquid-crystal forming compound is glyceryl monooleate.

129. A method according to claim 76, wherein the fatty acid combination is at least capric acid and lauric acid.

130. A therapeutic liquid or semisolid formulation, which forms a liquid crystalline state, the formulation comprising:
(i) from about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof;
(ii) solvent; and
(iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof in a therapeutically-effective amount, which is dissolved in the formulation.

131. An absorbent article comprising (a) an absorbent layer comprising a liquid-permeable and moisture vapor-permeable outer layer having an inner surface and an outer surface, the inner surface essentially coextensive with an outer surface of the absorbent layer; (b) a liquid-permeable liner, adapted to be non-adherent to a wound, having a surface that is substantially coextensive with an inner surface of the absorbent layer such that the absorbent layer is located between the liquid-permeable liner and the outer layer; and (c) a liquid or semisolid formulation, which forms a liquid crystalline state, present on at least a portion of a surface of the liquid-permeable liner opposite that which is coextensive with the inner surface of the outer layer, wherein the formulation comprises:
(i) from about 25% to about 99% by weight liquid-crystal forming compound, which is a fatty acid ester selected from the group consisting of glyceryl monoarachidonate, glyceryl monolinoleate, glyceryl monolinolenate, glyceryl monopalmitoleate, glyceryl monooleate, glyceryl monoerucate, propylene glycyl monoarachidonate, propylene glycyl monolinoleate, propylene glycyl monolinolenate, propylene glycyl monopalmitoleate, propylene glycyl monooleate, and combinations thereof;
(ii) solvent; and
(iii) a fatty acid combination selected from the group consisting of caprylic acid, capric acid, lauric acid, myristic acid, myristoleic acid, palmitic acid, palmitoleic acid, oleic acid, and pharmaceutically acceptable salts thereof, which is dissolved in the formulation.

132. A thrombin inhibitor formulation according to claim 11, wherein the liquid-crystal forming compound is at least glyceryl monooleate.

133. A thrombin inhibitor formulation according to claim 132, wherein the fatty acid combination is at least capric acid and lauric acid.

134. A thrombin inhibitor formulation according to claim 11, wherein the fatty acid combination is at least capric acid and lauric acid.

135. A medical cosmetic formulation according to claim 14, wherein the liquid-crystal forming compound is at least glyceryl monooleate.

136. A medical cosmetic formulation according to claim 135, wherein the fatty acid combination is at least capric acid and lauric acid.

137. A medical cosmetic formulation according to claim 14, wherein the liquid-crystal forming compound is glyceryl monooleate.

138. A medical cosmetic formulation according to claim 14, wherein the fatty acid combination is at least capric acid and lauric acid.

* * * * *